(12) United States Patent
Burenkova et al.

(10) Patent No.: US 10,184,006 B2
(45) Date of Patent: Jan. 22, 2019

(54) BIOMARKERS FOR PREDICTING OUTCOMES OF CANCER THERAPY WITH ERBB3 INHIBITORS

(71) Applicant: Merrimack Pharmaceuticals, Inc., Cambridge, MA (US)

(72) Inventors: Olga Burenkova, Newton, MA (US); Gavin MacBeath, Wakefield, MA (US); Lin Nie, Needham Heights, MA (US); Mark Sevecka, Cambridge, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/173,219

(22) Filed: Jun. 3, 2016

(65) Prior Publication Data

US 2017/0101480 A1    Apr. 13, 2017

Related U.S. Application Data

(60) Provisional application No. 62/171,062, filed on Jun. 4, 2015.

(51) Int. Cl.
| | |
|---|---|
| *C07K 16/32* | (2006.01) |
| *C12Q 1/6886* | (2018.01) |
| *C07K 16/30* | (2006.01) |
| *G01N 33/574* | (2006.01) |
| *A61K 39/00* | (2006.01) |

(52) U.S. Cl.
CPC ............ *C07K 16/32* (2013.01); *C07K 16/30* (2013.01); *C07K 16/3015* (2013.01); *C07K 16/3023* (2013.01); *C07K 16/3069* (2013.01); *C12Q 1/6886* (2013.01); *G01N 33/57407* (2013.01); *A61K 2039/505* (2013.01); *C07K 2317/21* (2013.01); *C07K 2317/565* (2013.01); *C07K 2317/76* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,183,884 | A | 2/1993 | Kraus et al. |
| 5,344,760 | A | 9/1994 | Harvey et al. |
| 5,480,968 | A | 1/1996 | Kraus et al. |
| 5,820,859 | A | 10/1998 | Kraus et al. |
| 5,916,755 | A | 6/1999 | Kraus et al. |
| 5,968,511 | A | 10/1999 | Akita et al. |
| 6,331,415 | B1 | 12/2001 | Cabilly et al. |
| 6,639,060 | B1 | 10/2003 | Kraus et al. |
| 6,696,290 | B2 | 2/2004 | Fitzpatrick et al. |
| 6,983,227 | B1 | 1/2006 | Thalhammer-Reyero |
| 7,097,840 | B2 | 8/2006 | Erickson et al. |
| 7,125,680 | B2 | 10/2006 | Singer et al. |
| 7,285,649 | B2 | 10/2007 | Akita et al. |
| 7,314,916 | B2 | 1/2008 | Singer et al. |
| 7,390,632 | B2 | 6/2008 | Maihle et al. |
| 7,449,184 | B2 | 11/2008 | Allison et al. |
| 7,589,180 | B2 | 9/2009 | Old et al. |
| 7,638,302 | B2 | 12/2009 | Maihle et al. |
| 7,638,303 | B2 | 12/2009 | Maihle et al. |
| 7,705,130 | B2 | 4/2010 | Rothe et al. |
| 7,846,440 | B2 | 12/2010 | Schoeberl et al. |
| 7,923,221 | B1 | 4/2011 | Cabilly et al. |
| 8,268,793 | B2 | 9/2012 | Hedtjam |
| 8,476,409 | B2 | 7/2013 | Baum et al. |
| 8,481,687 | B2 | 7/2013 | Vincent et al. |
| 8,623,592 | B2 | 1/2014 | Schoeberl et al. |
| 8,691,225 | B2 | 4/2014 | Schoeberl et al. |
| 8,877,687 | B2 | 11/2014 | Song et al. |
| 8,895,001 | B2 | 11/2014 | Moyo et al. |
| 8,927,694 | B2 | 1/2015 | McDonagh et al. |
| 8,961,966 | B2 | 2/2015 | Schoeberl et al. |
| 9,011,851 | B2 | 4/2015 | Ullrich et al. |
| 9,011,863 | B2 | 4/2015 | Aftab et al. |
| 9,101,760 | B2 | 8/2015 | Hellmann et al. |
| 9,228,021 | B2 | 1/2016 | Vincent et al. |
| 9,487,588 | B2 | 11/2016 | Schoeberl |
| 9,518,130 | B2 | 12/2016 | Moyo et al. |
| 9,688,761 | B2 | 6/2017 | Adiwijaya et al. |
| 2002/0001587 | A1 | 1/2002 | Erickson et al. |
| 2002/0002276 | A1 | 1/2002 | Fitzpatrick et al. |
| 2002/0009740 | A1 | 1/2002 | Kaddurah-Daouk et al. |
| 2002/0119148 | A1 | 8/2002 | Gerritsen et al. |
| 2002/0165193 | A1 | 11/2002 | Greene et al. |
| 2003/0040605 | A1 | 2/2003 | Siegel |
| 2003/0199020 | A1 | 10/2003 | Fitzpatrick et al. |
| 2004/0052786 | A1 | 3/2004 | Gerritsen et al. |
| 2004/0071696 | A1 | 4/2004 | Adams et al. |
| 2004/0082510 | A1 | 4/2004 | Ullrich et al. |
| 2004/0138417 | A1 | 7/2004 | Fitzpatrick et al. |
| 2004/0197332 | A1 | 10/2004 | Ullrich et al. |
| 2004/0229380 | A1 | 11/2004 | Chan-Hui et al. |
| 2004/0248151 | A1 | 12/2004 | Bacus et al. |
| 2004/0248196 | A1 | 12/2004 | Adams et al. |
| 2005/0004018 | A1 | 1/2005 | Jimeno et al. |
| 2005/0079184 | A1 | 4/2005 | Hsing-Chang et al. |
| 2005/0187745 | A1 | 8/2005 | Lurie et al. |
| 2005/0267720 | A1 | 12/2005 | Hill et al. |

(Continued)

FOREIGN PATENT DOCUMENTS

| | | |
|---|---|---|
| EP | 0896586 B1 | 2/1999 |
| EP | 1058562 B1 | 12/2000 |

(Continued)

OTHER PUBLICATIONS

Chen et al. (Molecular and Cellular Proteomics 1: 304-313, 2002).*

(Continued)

*Primary Examiner* — Nelson B Moseley, II
(74) *Attorney, Agent, or Firm* — Nelson Mullins Riley & Scarborough LLP; Jane E. Remillard, Esq.; Jill Gorny Sloper, Esq.

(57) ABSTRACT

Methods for predicting a therapeutic response in a patient (e.g., a cancer patient) to ErbB3 inhibitors, and methods of treating a cancer patient with targeted therapies.

18 Claims, 27 Drawing Sheets

Specification includes a Sequence Listing.

(56) References Cited

U.S. PATENT DOCUMENTS

| | | |
|---|---|---|
| 2006/0040363 A1 | 2/2006 | Kucherlapati et al. |
| 2006/0093603 A1 | 5/2006 | Gerritsen et al. |
| 2006/0127928 A1 | 6/2006 | Bacus et al. |
| 2006/0136139 A1 | 6/2006 | Elcock et al. |
| 2006/0167637 A1 | 7/2006 | Agur et al. |
| 2006/0177907 A1 | 8/2006 | Singer et al. |
| 2006/0204505 A1 | 9/2006 | Sliwkowski et al. |
| 2006/0210561 A1 | 9/2006 | Baughman et al. |
| 2007/0009972 A1 | 1/2007 | Chao et al. |
| 2007/0059785 A1 | 3/2007 | Bacus et al. |
| 2007/0081994 A1 | 4/2007 | Fitzpatrick et al. |
| 2007/0092513 A1 | 4/2007 | Gerritsen et al. |
| 2007/0122407 A1 | 5/2007 | Akita et al. |
| 2007/0134251 A1 | 6/2007 | Ashkenazi et al. |
| 2007/0134252 A1 | 6/2007 | Bacus et al. |
| 2007/0190583 A1 | 8/2007 | Spector et al. |
| 2007/0254295 A1 | 11/2007 | Harvey et al. |
| 2008/0026415 A1 | 1/2008 | Rimm et al. |
| 2008/0057064 A1 | 3/2008 | Zhou |
| 2008/0090233 A1 | 4/2008 | Garcia et al. |
| 2008/0112958 A1 | 5/2008 | Mass |
| 2008/0124334 A1 | 5/2008 | Akita et al. |
| 2008/0124345 A1 | 5/2008 | Rothe et al. |
| 2008/0172184 A1 | 7/2008 | Chaires et al. |
| 2008/0187948 A1 | 8/2008 | Chan-Hui et al. |
| 2008/0207615 A1 | 8/2008 | Bell et al. |
| 2008/0214584 A1 | 9/2008 | Ohta et al. |
| 2008/0254497 A1 | 10/2008 | Singh |
| 2008/0261270 A1 | 10/2008 | Maihle et al. |
| 2008/0274504 A1 | 11/2008 | Maihle et al. |
| 2008/0318894 A1 | 12/2008 | Hedtjarn |
| 2009/0061422 A1 | 3/2009 | Linke et al. |
| 2009/0181022 A1 | 7/2009 | Nielsen et al. |
| 2009/0246206 A1 | 10/2009 | Nielsen et al. |
| 2009/0291085 A1 | 11/2009 | Schoeberl et al. |
| 2010/0056761 A1 | 3/2010 | Schoeberl et al. |
| 2010/0158894 A1 | 6/2010 | Umemura et al. |
| 2010/0178651 A1 | 7/2010 | Hatzis et al. |
| 2010/0266584 A1 | 10/2010 | Schoeberl et al. |
| 2010/0310557 A1 | 12/2010 | Keyt et al. |
| 2011/0027291 A1 | 2/2011 | Schoeberl et al. |
| 2011/0033482 A1 | 2/2011 | Ullrich et al. |
| 2011/0123523 A1 | 5/2011 | Schoeberl et al. |
| 2011/0159513 A1 | 6/2011 | Schoeberl et al. |
| 2011/0171222 A1 | 7/2011 | Bossenmaier et al. |
| 2011/0229493 A1 | 9/2011 | Jackson et al. |
| 2011/0256154 A1 | 10/2011 | Vincent et al. |
| 2012/0015827 A1 | 1/2012 | Wirtz |
| 2012/0156130 A1 | 6/2012 | Hettmann et al. |
| 2012/0225870 A1 | 9/2012 | Janne et al. |
| 2012/0244163 A1 | 9/2012 | Schoeberl et al. |
| 2013/0034548 A1 | 2/2013 | Moyo et al. |
| 2013/0236459 A1 | 9/2013 | Baum et al. |
| 2013/0259867 A1 | 10/2013 | Amler et al. |
| 2014/0017264 A1 | 1/2014 | McDonagh et al. |
| 2014/0056898 A1 | 2/2014 | Zhang et al. |
| 2014/0079703 A1 | 3/2014 | Zhang et al. |
| 2014/0127238 A1 | 5/2014 | Schoeberl et al. |
| 2014/0134170 A1 | 5/2014 | Garcia et al. |
| 2014/0234317 A1 | 8/2014 | Onsum et al. |
| 2014/0234329 A1 | 8/2014 | Schoeberl et al. |
| 2014/0242597 A1 | 8/2014 | Vincent et al. |
| 2014/0248280 A1 | 9/2014 | Kubasek et al. |
| 2014/0271665 A1 | 9/2014 | Aftab et al. |
| 2014/0273006 A1 | 9/2014 | Singh et al. |
| 2015/0132292 A1 | 5/2015 | Moyo et al. |
| 2015/0147326 A1 | 5/2015 | Schneider et al. |
| 2015/0152508 A1 | 6/2015 | Schneider et al. |
| 2015/0231238 A1 | 8/2015 | Garcia et al. |
| 2016/0090418 A1 | 3/2016 | Adiwijaya et al. |
| 2016/0303232 A1 | 10/2016 | Adiwijaya et al. |
| 2017/0073427 A1 | 3/2017 | Schoeberl et al. |
| 2017/0210810 A1 | 7/2017 | Adiwijaya et al. |
| 2017/0267767 A1 | 9/2017 | Adiwijaya et al. |
| 2017/0291957 A1 | 10/2017 | Moyo et al. |
| 2017/0307631 A1 | 10/2017 | Schoeberl et al. |

FOREIGN PATENT DOCUMENTS

| | | |
|---|---|---|
| EP | 1187634 B1 | 3/2002 |
| EP | 1283053 A1 | 2/2003 |
| EP | 1351744 B1 | 10/2003 |
| EP | 1414494 B1 | 5/2004 |
| EP | 1728802 A2 | 12/2006 |
| EP | 1889631 A1 | 2/2008 |
| EP | 2067792 A2 | 6/2009 |
| EP | 2138511 A1 | 12/2009 |
| EP | 2764364 A1 | 8/2014 |
| WO | 97/35885 A1 | 10/1997 |
| WO | 98/02540 A1 | 1/1998 |
| WO | 99/54800 A2 | 10/1999 |
| WO | 99/60023 A1 | 11/1999 |
| WO | 00/78347 A1 | 12/2000 |
| WO | 02/18444 A2 | 3/2002 |
| WO | 02060470 A1 | 8/2002 |
| WO | 03012072 A2 | 2/2003 |
| WO | 03013602 A1 | 2/2003 |
| WO | 2004/003019 A3 | 1/2004 |
| WO | 2004/008099 A2 | 1/2004 |
| WO | 2004/053497 A2 | 6/2004 |
| WO | 2004/091384 A2 | 10/2004 |
| WO | 2004/094386 A1 | 11/2004 |
| WO | 2005/017493 A2 | 2/2005 |
| WO | 2005/046678 A1 | 5/2005 |
| WO | 2006/017538 A2 | 2/2006 |
| WO | 2006/020706 A2 | 2/2006 |
| WO | 2006/044748 A2 | 4/2006 |
| WO | 2006/063042 A2 | 6/2006 |
| WO | 2006/091209 A2 | 8/2006 |
| WO | 2007/015935 A2 | 2/2007 |
| WO | 2007/039705 A1 | 4/2007 |
| WO | 2007/041502 A2 | 4/2007 |
| WO | 2007/077028 A2 | 7/2007 |
| WO | 2007/115571 A2 | 10/2007 |
| WO | 2007/130677 A2 | 11/2007 |
| WO | 2008/032876 A1 | 3/2008 |
| WO | 2008/064884 A1 | 6/2008 |
| WO | 2008/100624 A2 | 8/2008 |
| WO | 2008/109440 A2 | 9/2008 |
| WO | 2009/027332 A1 | 3/2009 |
| WO | 2009/126920 A2 | 10/2009 |
| WO | 2009/156179 A1 | 12/2009 |
| WO | 2010/019952 A2 | 2/2010 |
| WO | 2010/059315 A1 | 5/2010 |
| WO | 2010/127181 A1 | 11/2010 |
| WO | 2011/022727 A2 | 2/2011 |
| WO | 2011/044311 A2 | 4/2011 |
| WO | 2011/047180 A1 | 4/2011 |
| WO | 2011/112953 A2 | 9/2011 |
| WO | 2011/163466 A1 | 12/2011 |
| WO | 2012/019952 A1 | 2/2012 |
| WO | 2012/103341 A1 | 8/2012 |
| WO | 2012/125573 A2 | 9/2012 |
| WO | 2012/125864 A2 | 9/2012 |
| WO | 2012145507 A2 | 10/2012 |
| WO | 2012/154587 A2 | 11/2012 |
| WO | 2012/177440 A1 | 12/2012 |
| WO | 2013/023043 A2 | 2/2013 |
| WO | 2013/033623 A1 | 3/2013 |
| WO | 2013/052745 A1 | 4/2013 |
| WO | 2013/086031 A1 | 6/2013 |
| WO | 2013/152034 A1 | 10/2013 |
| WO | 2015/048793 A2 | 4/2015 |
| WO | 2015/100459 A2 | 7/2015 |
| WO | 2015/130554 A2 | 9/2015 |
| WO | 2016/168730 A1 | 10/2016 |

OTHER PUBLICATIONS

Aaronson, S.A. et al., "Growth factor-regulated pathways in epithelial cell proliferation," Am. Rev. Respir. Dis., vol. 142(6 pt. 2):S7-S10 (1990).

(56) References Cited

OTHER PUBLICATIONS adapt, The Peterson Institute for Cancer Research, Probesets for Betacellulin (BTC), 2 pages (2013).
adapt, The Peterson Institute for Cancer Research, Probesets for ErbB1(EGFR), 4 pages (2013).
adapt, The Peterson Institute for Cancer Research, Probesets for ErbB2, 3 pages (2013).
adapt, The Peterson Institute for Cancer Research, Probesets for ErbB3, 3 pages (2013).
adapt, The Peterson Institute for Cancer Research, Probesets for neuregulin (NRG1), 14 pages (2013).
Alberts, Bruce et al., Molecular Biology of the Cell, Third Edition, Garland Publishing, Inc., New York, pp. 897-899 (1994).
Alimandi, Maurizio et al., "Cooperative signaling of ErbB3 and ErbB2 in neoplastic transformation and human mammary carcinomas," Oncogene, vol. 10:1813-1821 (1995).
Alimandi, Maurizio et al., "Epidermal growth factor and betacellulin mediate signal transduction through co-expressed ErbB2 and ErbB3 receptors," The EMBO Journal, vol. 16(18):5608-5617 (1997).
Arnedos, M. et al., "A Phase 1 Study of MM-121 in Combination with Multiple Anticancer Therapies in Patients with Advanced Solid Tumors," ASCO, 1 page (2013).
ATCC, "AdrR," retrieved online at: http://www.atcc.org/ATCCAdvancedCatalogSearch/AllCollectionSearch/tabid/454/Default.aspx, 1 page (2011).
Atlas, E. et al., "A Deletion Mutant of Heregulin Increases the Sensitivity of Breast Cancer Cells to Chemotherapy without Promoting Tumorigenicity," Oncogene, vol. 22: 3441-3451 (2003).
Aurisicchio, L. et al., "The promise of anti-ErbB3 monoclonals as new cancer therapeutics," Oncotarget, August, vol. 3(8):744-758 (2012).
Bae, S. et al., "HER3 status by immunohistochemistry is correlated with poor prognosis in hormone receptor-negative breast cancer patients," Breast Cancer Res. Treat, vol. 139: 741-750 (2013).
Balint, Robert F. et al., "Antibody engineering by parsimonious mutagenesis," Gene, vol. 137:109-118 (1993).
Baselga, Jose et al., "Novel anticancer targets: revisiting ERBB2 and discovering ERBB3," Nature Reviews Cancer, vol. 9(7):463-475 (2009).
Baselga, Jose et al., "Phase II Trial of Pertuzumab and Trastuzumab in Patients With Human Epidermal Growth Factor Receptor 2-Positive Metastatic Breast Cancer That Progressed During Prior Trastuzumab Therapy," Journal of Clinical Oncology, vol. 28(7):1138-1144 (2010).
Bazdar-Vinovrski, B. et al., "A Phase 1 biomarker-directed multi-arm study evaluating the co-administration of MM-151 with seribantumab (MM-121), istiratumab (MM-141), or trametinib in EGFR-driven cancers," ASCO, Abstract No. TPS11619 I pages (2016).
Becerril, Baltazar et al., "Toward Selection of Internalizing Antibodies from Phage Libraries," Biochemical and Biophysical Research Communications, vol. 255:386-393 (1999).
Beckman, Robert A. et al., "Antibody Constructs in Cancer Therapy, Protein Engineering Strategies to Improve Exposure in Solid Tumors," Cancer, vol. 109:170-179 (2007).
Beerli, Roger R. et al., "Neu Differentiation Factor Activation of ErbB-3 and ErbB-4 is Cell Specific and Displays a Differential Requirement for ErbB-2," Molecular and Cellular Biology, vol. 15(12):6496-6505 (1995).
Bes C. et al., "Mapping the paratope of anti-CD4 recombinant Fab 13B8.2 by combining parallel peptide synthesis and site-directed mutagenesis", Journal of Biological Chemistry, vol. 278 (16):14265-14273 (2003).
Biomarkers Definitions Working Group, "Biomarkers and surrogate endpoints: Preferred definitions and conceptual framework," Clinical Pharmacology and Therapeutics, vol. 69(3): 89-95 (2001).
Board, RE, et at., "Multiplexed assays for detection of mutations in PIK3CA," Clin. Chem., 54(4):757-760 (2008).

Bodey, Bela et al., "Immunophenotypically Varied Cell Subpopulations in Primary and Metastatic Human Melanomas. Monoclonal Antibodies for Diagnosis, Detection of Neoplastic Progression and Receptor Directed Immunotherapy," Anticancer Research, vol. 16:517-532 (1996).
Bortoletto, Nicola et al., "Optimizing anti-CD3 affinity for effective T cell targeting against tumor cells," Eur. J. Immunol., vol. 32:3102-3107 (2002).
Bostwick, David G., "c-erbB-2 Oncogene Expression in Prostatic Intraepithelial Neoplasia: Mounting Evidence for a Precursor Role," Journal of the National Cancer Institute, vol. 86(15):1108-1110 (1994).
Brand, Francois-Xavier et al., "Prospect for anti-HER2 Receptor Therapy in Breast Cancer," Anticancer Research, vol. 26:463-470 (2006).
Breuleux, M., "Role of Heregulin in Human Cancer," Cell. Mol. Life. Sci., vol. 64:2358-2377 (2007).
Brodie, Angela et al., "Adaptive changes result in activation of alternate signaling pathways and acquisition of resistance to aromatase inhibitors," Clin. Cancer Res., vol. 17(13):4208-4213 (2011).
Brorson, Kurt et al., "Mutational Analysis of Avidity and Fine Specificity of Anti-Levan Antibodies," The Journal of Immunology, vol. 163:6694-6701 (1999).
Brotherick, Ian et al., "A flow cytometric study of c-erbB-3 expression in breast cancer," Cancer Immunol. Immunother., vol. 41:280-286 (1995).
Brown, McKay et al., "Tolerance to Single, but Not Multiple, Amino Acid Replacements in Antibody VH CDR2," The Journal of Immunology, vol. 156:3285-3291 (1996).
Burenkova, O. et al., "In vivo effect of combination therapy. An anti ErbB3 antibody, MM121, plus selected cancer therapies," Proceedings of the American Associarion for Cancer Research, Annual Meeting, vol. 50, Apr. 2009 (Apr. 2009), 2 pages, Abstract 1243.
Campbell, Marcia R. et al., "HER3 Comes of Age: New Insights into its Functions and Role in Signaling, Tumor Biology, and Cancer Therapy," Clin. Cancer Res., vol. 16(5):1373-1383 (2010).
Carraway, Kermit L. III et al., "A Neu Acquaintance for ErbB3 and ErbB4: A Role for Receptor Heterodimerization in Growth Signaling," Cell, vol. 78:5-8 (1994).
Carraway, Kermit L. III et al., "Heregulin Stimulates Mitogenesis and Phosphatidylinositol 3-Kinase in Mouse Fibroblasts Transfected with erbB2/neu and erbB3," The Journal of Biological Chemistry, vol. 270(13):7111-7116 (1995).
Carraway, Kermit L. III et al., "The erbB3 Gene Product is a Receptor for Heregulin," The Journal of Biological Chemistry, vol. 269(19):14303-14306 (1994).
Chan, Andrew C. et al., "Therapeutic antibodies for autoimmunity and inflammation," Nature Reviews Immunology, vol. 10:301-316 (2010).
Chen, Xiaomei et al., "An Immunological Approach Reveals Biological Differences between the Two NDF/Heregulin Receptors, ErbB-3 and ErbB-4," The Journal of Biological Chemistry, vol. 271(13):7620-7629 (1996).
Cho, "Contribution of oncoproteomics to cancer biomarker discovery," Molecular Cancer, vol. 6 (25):13 pages (2007).
Ciardiello, Fortunato et al., "Differential expression of epidermal growth factor-related proteins in human colorectal tumors," Proc. Natl. Acad. Sci. USA, vol. 88:7792-7796 (1991).
Cicenas, J. et al, "Phosphorylation of tyrosine 1248-ERBB2 measured by chemiluminescence-linked immunoassay is an independent predictor of poor prognosis in primary breast cancer patients," European J Cancer, vol. 42:636-645 (2006).
Cleary, J.M., "A Phase 1 Study of MM-121 (a fully human monoclonal antibody targeting the epideral growth factor receptor family member ErbB3) in Combination with Cetuximab and Irinotecan in Patients with Advanced Cancers," American Society of Clinical Oncology, 2014, Poster Presentation, 1 page.
Curley, M et al., "MM-121/SAR256212, an anti-ErbB3 antibody, restores sensitivity to letrozole and delays the onset of resistance in an ER+ breast cancer model," Merrimack Pharmaceuticals & Sanofi, Apr. 1, 2013, Poster Presentation, pp. 1-22.

(56) References Cited

OTHER PUBLICATIONS

Curley, MD et al., "Seribantumab, an Anti-ERBB3 Antibody, Delays the Onset of Resistance and Restores Sensitivity to Letrozole in an Estrogen Receptor-Positive Breast Cancer Model," Mol. Cancer Ther., vol. Pages (2015).
Curley, Michael "MM-121, an anti-ErbB3 antibody, inhibits PI3K/AKT signaling and viability in platinum-resistant ovarian cells and in primary ascites derived from chemo-resistant ovarian cancer patients," European Organisation for Research and Treatment of Cancer (EORTC), 2012,Poster No. 108, p. 1.
Denlinger, C.S. et al., "A phase I/II and pharmacologic study of MM-111 in patients with advanced, refractory HER2-positive (HER2+) cancers," J. Clin. Oncol., vol. 28(15s), 2010 ASCO Annual Meeting, Abstract No. TPS169, 4 pages (2010).
Denlinger, C.S. et al., "Phase I Dose escalation Study of MM-121, a Fully Human Monoclonal Antibody to ErbB3, in Patients with Advanced Solid Tumors," American Association for Cancer Research (AACR) Annual meeting, 2011, 1 page.
Dennis, Carina, "Off by a whisker," Nature, vol. 442:739-741 (2006).
Jiang, B. et al., "A novel peptide isolated from a phage display peptide library with trastuzumab can mimic antigen epitope of HER-2," J. Biol. Chem., vol. 280 (6): 4656-4662 (2005).
Press, OW et al., "Ricin A-chain containing immunotoxins directed against different epitopes on the CD2 molecule differ in their ability to kill normal and malignant T cells," J. Immunol., vol. 141 (12): 4410-4417 (1988).
Riemer, AB et al., "Matching of trastuzumab (Herceptin) epitope mimics onto the surface of Her-2/neu—a new method of epitope definition," Mol. Immunol., vol. 42(9): 1121-1124 (2005).
Slamon, Dennis J. et al., "Human Breast Cancer: Correlation of Relapse and Survival with Amplification of the HER-2/neu Oncogene," Science, vol. 235:177-182 (1987).
Slamon, Dennis J. et al., "Studies of the HER-2/neu Proto-oncogene in Human Breast and Ovarian Cancer," Science, vol. 244:707-712 (1989).
Sliwkowski, Mark X. et al., "Coexpression of erbB2 and erbB3 Proteins Reconstitutes a High Affinity Receptor for Heregulin," The Journal of Biological Chemistry, vol. 269(2):14661-14665 (1994).
Smith, B.L. et al., "The efficacy of Herceptin therapies is influenced by the expression of other erbB receptors, their ligands and the activation of downstream signalling proteins," British Journal of Cancer, vol. 91:1190-1194 (2004).
Smith-Gill, Sandra J. et al., "Contributions of Immunoglobulin Heavy and Light Chains to Antibody Specificity for Lysozyme and Two Haptens," The Journal of Immunology, vol. 139:4135-4144 (1987).
Soltoff, Stephen P. et al., "ErbB3 is Involved in Activation of Phosphatidylinositol 3-Kinase by Epidermal Growth Factor," Molecular and Cellular Biology, vol. 14(6):3550-3558 (1994).
Sonne-Hansen, Katrine et al., "Breast cancer cells can switch between estrogen receptor alpha and ErbB signaling and combined treatment against both signaling pathways postpones development of resistance," Breast Cancer Res. Treat., vol. 121:601-613 (2010).
Specht et al. (American Journal of Pathology, 158(2):419-429 (2001).
Surmacz, Eva, "Growth factor receptors as therapeutic targets: strategies to inhibit the insulin-like growth factor I receptor," Oncogene, vol. 22:6589-6597 (2003).
Tamimi et al. (Cancer Research, 53:5512-5516 (1993).
Third Party Observations dated Jan. 16, 2015, filed in European Patent Application No. 12775896(EP2764364) (2 pages).
Tzahar, Eldad et al., "A Hierarchical Network of Interreceptor Interactions Determines Signal Transduction by Neu Differentiation Factor/Neuregulin and Epidermal Growth Factor," Molecular and Cellular Biology, vol. 16(10):5276-5287 (1996).
Tzahar, Eldad et al., "ErbB-3 and ErbB-4 Function as the Respective Low and High Affinity Receptors of All Neu Differentiation Factor/Heregulin Isoforms," The Journal of Biological Chemistry, vol. 269(40):25226-25233 (1994).

Ullrich, Axel et al., "Signal Transduction by Receptors with Tyrosine Kinase Activity," Cell, vol. 61:203-212 (1990).
Vaidya, Pradeep et al., "Overexpression of Different Members of the Type 1 Growth Factor Receptor Family and Their Association with Cell Proliferation in Periampullary Carcinoma," Journal of Pathology, vol. 178:140-145 (1996).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).
Wainszelbaum, Marisa et al., "In vitro studies of MM-121/SAR 256212, an anti-ErbB-3 antibody, in combination with erlotinib; in EGFR-wild-type NSCLC," AARC Meeting 2013, Poster 5464, p. 1.
Wallasch, Christian et al., "Heregulin-dependent regulation of HER2/neu oncogenic signaling by heterodimerization with HER3," The EMBO Journal, vol. 14(17):4267-4275 (1995).
Wang, S. et al., "Therapeutic Targeting of ErbB3 with MM-121/Sar256212 enchances antitumor activity of paclitaxel against erbB2-overexpressing breast cancer," Breast Cancer Research, vol. 15(5): R101 (2013).
Wilson TR et al., 'Neuregulin-1-Mediated Autocrine Signaling Underlies Sensitivity to HER2; Kinase Inhibitors in a Subset of Human Cancers,' Cancer Cell, Aug. 16, 2011 (Aug. 16, 2011), vol. 20(2):158-172.
Wingens, Miriam et al., "Structural Analysis of an Epidermal Growth Factor/Transforming Growth Factor-a Chimera with Unique ErbB Binding Specificity," The Journal of Biological Chemistry, vol. 278(40):39114-39123 (2003).
Wu, Dianging et al., "Human Epidermal Growth Factor (EGF) Receptor Sequence Recognized by EGF Competitive Monoclonal Antibodies," The Journal of Biological Chemistry, vol. 264(29):17469-17475 (1989).
Wu, Herren et al., "Humanization of a Murine Monoclonal Antibody by Simultaneous Optimization of Framework and CDR Residues," J. Mol. Biol., vol. 294:151-162 (1999).
Yarar, D. et al., "Heregulin-ErbB3-driven tumour growth persists in PI3 Kinase Mutant Cancer Cells," Mol. Cancer Ther., vol. 14(9):2072-2080 (2015).
Ye, Dingwei et al., "Augmentation of a humanized Anti-HER2 mAb 4D5 induced growth inhibition by a human-mouse chimeric anti-EGF receptor mAb C225," Oncogene, vol. 18:731-738 (1999).
Zelada-Hedman, Moraima et al., "High Expression of the EGFR in Fibroadenomas Compared to Breast Carcinomas," Anticancer Research, vol. 14:1679-1688 (1994).
Zhang, Ke et al., "Transformation of NIH 3T3 Cells by HER3 or HER4 Receptors Requires the Presence of HER1 or HER2," The Journal of Biological Chemistry, vol. 271(7):3884-3890 (1996).
Zhou, BB et al., 'Targeting ADAM-Mediated Ligand Cleavage to Inhibit HER3 and EGFR Pathways; in Non-Small Cell Lung Cancer,' Cancer Cell, Jul. 2006 (Jul. 2006), 10(1 ):39-50.
Brummell, David A. et al., "Probing the Combining Site of an Anti-Carbohydrate Antibody by Saturation-Mutagenesis: Role of the Heavy-Chain CDR3 Residues," Biochemistry, vol. 32:1180-1187 (1993).
Burks, Elizabeth A. et al., "In vitro scanning saturation mutagenesis of an antibody binding pocket," Proc. Natl. Acad. Sci. USA, vol. 94:412-417 (1997).
Casset, Florence et al., "A peptide mimetic of an anti-CD4 monoclonal antibody by rational design," Biochemical and Biophysical Research Communications, vol. 307:198-205 (2003).
Cespedes, Maria Virtudes et al., "Mouse models in oncogenesis and cancer therapy," Clin. Transl. Oncol., vol. 8(5):318-329 (2006).
Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).
Colman, P.M., "Effects of amino acid sequence changes on antibody-antigen interactions," Research in Immunology, vol. 145:33-36 (1994).

(56) References Cited

OTHER PUBLICATIONS

Communication Pursuant to Article 94(3) EPC in European Patent Application No. 12775896 (EP2764364) dated Apr. 1, 2015 (5 pages).
Davies, Jullian et al., "Affinity improvement of single antibody VH domains: residues in all three hypervariable regions affect antigen binding," Immunotechnology, vol. 2:169-179 (1996).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Dufner, Patrick et al., "Harnessing phage and ribosome display for antibody optimisation," Trends in Biotechnology, vol. 24(11):523-529 (2006).
European Search Report and Written Opinion for Application No. 13180584.8, 14 pages, dated Jun. 13, 2014.
Excerpt Wikipedia re Cetuximab, accessed Oct. 12, 2015.
Fontayne A. et al., "Paratope and epitope mapping of the antithrombotic antibody 6B4 in complex with platelet glycoprotein 1b alpha," Journal of Biologival Chemistry, vol. 282 (32) :23517-23524 (2007).
Francois, Christine et al., "Antibodies directed at mouse II-2-R a and b chains act in synergy to abolish T-cell proliferation in vitro and delayed type hypersensitivity reaction in vivo," Transpl. Int., vol. 9:46-50 (1996).
Gasparini, G. et al., "Randomized phase II trial of weekly paclitaxel alone verus trastuzumab plus weekly paclitaxel as; first-line therapy of patients with Her-2 positive advanced breast cancer," Breast Cancer Res. Treat., vol. 101, pp. 355-365 (2007).
Gown, Allen M., "Current issues in ER and HER2 testing by Ihc in breast cancer," Modern Pathology, vol. 21:S8-S15 (2008).
Guddat LW et al.: Three-dimensional structure of human immunoglobulin with a hinge deletion», Proceedings of the National Academy of Sciences, National Academy of Sciences, US, vol. 90, May 1, 1993 (May 1, 1993), pp. 4271-4275.
Guy, Pamela M. et al., "Insect cell-expressed p180erbB3 possesses an impaired tyrosine kinase activity," Proc. Natl. Acad. Sci. USA, vol. 91:8132-8136 (1994).
Hellyer, Nathan J. et al., "Cloning of the rat ErbB3 cDNA and characterization of the recombinant protein," Gene, vol. 165:279-284 (1995).
Hofmann, Francesco et al., "Blocking insulin-like growth factor-I receptor as a strategy for targeting cancer," DDT, vol. 10(15):1041-1047 (2005).
Holm, Patrik et al., "Functional mapping and single chain construction of the anti-cytokeratin 8 monoclonal antibody TS1," Molecular Immunology, vol. 44:1075-1084 (2007).
Holmes, William E. et al., "Identification of Heregulin, a Specific Activator of p185erbB2," Science, vol. 256:1205-1210 (1992).
Holt, Lucy J. et al., "Domain antibodies: proteins for therapy," Trends in Biotechnology, Vo. 21(11):484-490 (2003).
Huse, et al., "Generation of a large combinatorial library of the immunoglobulin repertoire in phage lambda," Science 246: 1275-1281 (1989).
Information Disclosure Submission concerning Agreement between Dyax Corporation and Merrimack Pharmaceuticals, Jun. 30, 2010.
Invitation to Pay Additional Fees for Application No. PCT/US2008/002119, dated Oct. 7, 2008.
Irvin, W. et al., "What is triple-negative breast cancer?" European Journal of Cancer, vol. 44, pp. 2799-2805 (2008).
Jang, Y.-J. et al., "The structural basis for DNA binding by an anti-DNA auto antibody," Molecular Immunology, vol. 35:1207-1217 (1998).
Janku, F., et al., "PIK3CA mutations in patients with advanced cancers treated with PI3K/AKT/mTOR axis inhibitors," Mol. Cancer Ther., 10(3): 558-565 (2011).
Jeschke, Margit et al., "Targeted Inhibition of Tumor-cell Growth by Recombinant Heregulin-toxin Fusion Proteins," Int. J. Cancer, vol. 60:730-739 (1995).

Jo, Sangmee Ahn et al., "Neuregulins are concentrated at nerve-muscle synapses and activate ACh-receptor gene expression," Nature, vol. 373:158-161 (1995).
Kinugasa, Yumi et al., "Neuroglycan C, a novel member of the neuregulin family," Biochemical and Biophysical Research Communications, vol. 321:1045-1049 (2004).
Kita, Yoshiko et al., "Bioactive Synthetic Peptide of NDF/Heregulin," Biochemical and Biophysical Research Communicatnions, vol. 210(2):441-451 (1995).
Kobayashi, Hiroyuki et al., "Tryptophan H33 plays an important role in pyrimidine (6-4) pyrimidone photoproduct binding by a high-affinity antibody," Protein Engineering, vol. 12(10):879-884 (1999).
Kohler, "Derivation of specific antibody-producing tissue culture and tumor lines by cell fusion," Eur. J. Immunol. 6(7): 511-; 519 (1976).
Kumar, Sanjeev et al., "Molecular Cloning and Expression of the Fabs of Human Autoantibodies in *Escherichia coli*," The Journal of Biological Chemistry, vol. 275(45):35129-35136 (2000).
Lederman, Seth et al., "A Single Amino Acid Substitution in a Common African Allele of the CD4 Molecule Ablates Binding of the Monoclonal Antibody, OKT4," Molecular Immunology, vol. 28(11):1171-1181 (1991).
Levi, Allan D.O. et al., "The Influence of Heregulins on Human Schwann Cell Proliferation," The Journal of Neuroscience, vol. 15(2):1329-1340 (1995).
Li, Choh Hao et al., "Beta-Endorphin omission analogs: Dissociation of immunoreactivity from other biological activities," Proc. Natl. Acad. Sci. USA, vol. 77(6):3211-3214 (1980).
Li, Yu, et al., Expression and Activity of Carbonic Anhydrase IX is Associated With Metabolic Dysfunction in MDA-MB-231 Breast Cancer Cells, Cancer Investigation, vol. 27: 613-623 (2009).
Little, M. et al., "Of mice and men: hybridoma and recombinant antibodies," Immunology Today, vol. 21(8):364-370 (2000).
Lu, Dan et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Research, vol. 61:7002-7008 (2001).
MacCallum, Robert M. et al., "Antibody-antigen Interactions: Contact Analysis and Binding Site Topography," J. Mol. Biol., vol. 262:732-745 (1996).
Marchionni, Mark A. et al., "Glial growth factors are alternatively spliced erbB2 ligands expressed in the nervous system," Nature, vol. 362:312-318 (1993).
Markman, M. et al., "Phase II trial of weekly paclitaxel (80 mg/m2) in platinum and paclitaxel-resistant ovarian and primary peritoneal cancers: a gynecologic oncology group study," Gyncol. Oncol., vol. 101, pp. 436-440 (2006).
McCall, Adrian M. et al., "Increasing the Affinity for Tumor Antigen Enhances Bispecific Antibody Cytotoxicity," The Journal of Immunology, vol. 166:6112-6117 (2001).
Morrissey, Thomas K. et al., "Axon-induced mitogenesis of human Schwann cell involves heregulin and p185erbB2," Proc. Natl. Acad. Sci. USA, vol. 92:1431-1435 (1995).
Nielsen, Ulrik B. et al., "Targeting of Bivalent Anti-ErbB2 Diabody Antibody Fragments to Tumor Cells is Independent of the Intrinsic Antibody Affinity," Cancer Research, vol. 60:6434-6440 (2000).
Orr-Urtreger, Avi et al., "Neural expression and chromosomal mapping of Neu differentiation factor to 8p12-p21," Proc. Natl. Acad. Sci. USA, vol. 90:1867-1871 (1993).
Padlan, E.A., "X-Ray Crystallography of Antibodies," Advance Protein Chemistry, vol. 49:57-133 (1996).
U.S. Appl. No. 15/601,955, filed May 22, 2017, Bambang Adiwijaya.
U.S. Appl. No. 15/156,603, Jul. 20, 2017, M. Natarajan.
U.S. Appl. No. 14/967,158, Sep. 29, 2017, S. Rawlings.
U.S. Appl. No. 15/173,219, Jul. 6, 2017, N. Moseley.
U.S. Appl. No. 15/274,989, Nov. 3, 2017, L. Bristol.
Di Fiore, Pier Paolo et al., "Mechanisms involving an expanding erbB/EGF receptor family of tyrosine kinases in human neoplasia," Genes, Oncogenes, and Hormones, Robert B. Dickson, Ed., Kluwer Academic Publishers, pp. 139-160 (1992).

(56) References Cited

OTHER PUBLICATIONS

Dorvillius, Mylene et al., "Targeting of Human Breast Cancer by a Bispecific Antibody Directed against Two Tumour-Associated Antigens: ErbB-2 and Carcinoembryonic Antigen," Tumor Biol., vol. 23:337-347 (2002).
Drebin, Jeffrey A. et al., "Monoclonal antibodies reactive with distinct domains of the neu oncogene-encoded p185 molecule exert synergistic anti-tumor effects in vivo," Oncogene, vol. 2:273-277 (1988).
Eccles, Suzanne A. et al., "Significance of the c-erbB Family of Receptor Tyrosine Kinases in Metastatic Cancer and Their Potential as Targets for Immunotherapy," Invasion Metastasis, vol. 14:337-348 (1995).
Engelman, et al. "The role of the ErbB family members in non-small cell lung cancers sensitive to epidermal growth factor receptor kinase inhibitors," Clinical Cancer Research, vol. 12:4372s-4376s (2006).
Engelman, Jeffrey A. et al., "MET Amplification Leads to Gefitinib Resistance in Lung Cancer by Activating ERBB3 Signaling," Science, vol. 316:1039-1043 (2007).
Erjala, Kaisa et al., "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells," Clin. Cancer Res., vol. 12(13):4103-4111 (2006).
Esteva, Francisco J. et al., "Expression of erbB/HER Receptors, Heregulin and P38 in Primary Breast Cancer using Quantitative Immunohistochemistry," Pathology Oncology Research, vol. 7(3):171-177 (2001).
Ethier, Stephen P. et al., "erbB Family Receptor Expression and Growth Regulation in a Newly Isolated Human Breast Cancer Cell Line," Cancer Research, vol. 56:899-907 (1996).
Faksvåg, Dagny R. et al., "Expression of c-erbB-3 and c-erbB-4 Proteins in Papillary Thyroid Carcinomas," Cancer Research, vol. 56:1184-1188 (1996).
Fendly, Brian M. et al., "Characterization of Murine Monoclonal Antibodies Reactive to Either the Human Epidermal Growth Factor Receptor or HER2/neu Gene Product," Cancer Research, vol. 50:1550-1558 (1990).
Fiddes, Rodney J. et al., "Heregulin (HRG)-induced Mitogenic Signaling and Cytotoxic Activity of a HRG/PE40 Ligand Toxin in Human Breast Cancer Cells," Cell Growth & Differentiation, vol. 6:1567-1577 (1995).
Finn, G. et al., "A Randomized Trial of Exemestane +/− Seribantumab (MM-121) in Postmenopausal Women With Locally Advanced or Metastatic ER/PR+ HER2—Breast Cancer: Final Analysis and Extended Subgroup Analysis," AACR Miami, 1 page (2016).
Fitzgerald, JB, et al., "MM-141, an IGF-IR- and ErbB3-directed bispecific antibody, overcomes network adaptations that limit activity of IGF-IR inhibitors," Mol. Cancer Ther., vol. 13(2): 410-425 (2014).
Fitzpatrick, V. Danial et al., "Formation of a high affinity heregulin binding site using the soluble extracellular domains of ErbB2 with ErbB3 or ErbB4," FEBS Letters, vol. 431:102-106 (1998).
Foley, John et al., "EGFR Signaling in Breast Cancer: Bad to the Bone," Semin. Cell. Dev. Biol., vol. 21(9):951-960 (2010).
Friess, H. et al., "Pancreatic cancer: the potential clinical relevance of alterations in growth factors and their receptors," J. Mol. Med., vol. 74:35-42 (1996).
Friess, Helmut et al., "Enhanced erbB-3 Expression in Human Pancreatic Cancer Correlates with Tumor Progression," Clinical Cancer Research, vol. 1:1413-1420 (1995).
Frogne, Thomas et al., "Activation of ErbB3, EGFR and Erk is essential for growth of human breast cancer cell lines with acquired resistance to fulvestrant," Breast Cancer Res. Treat., vol. 114(2):263-275 (2009).
Fuchs, C.S. "Gastric Carcinoma," The New England Journal of Medicine, vol. 333(21):1426-1428 (1995).
Fujimori, Kenji et al., "A Modeling Analysis of Monoclonal Antibody Percolation Through Tumors: A Binding-Site Barrier," J. Nucl. Med., vol. 31:1191-1198 (1990).
Gamett, Daniel C. et al., "Heregulin-stimulated Signaling in Rat Pheochromocytoma Cells," The Journal of Biological Chemistry, vol. 270(32):19022-19027 (1995).
Garner et al., "An antibody that locks HER3 in the inactive conformation inhibits tumor growth driven by; HER2 or neuregulin," Cancer Research, vol. 73, No. 19, Aug. 2013, pp. 6024-6035.
Gorgoulis, V. et al., "Molecular and immunohistochemical study of class I growth factor receptors in squamous cell lung carcinomas," Abstracts / Lung Cancer, vol. 14:381 (1996).
Grasso, Adam W. et al., "ErbB kinases and NDF signaling in human prostate cancer cells," Oncogene, vol. 15:2705-2716 (1997).
Gullick, W.J., "The c-erbB3/HER3 Receptor in Human Cancer," Cancer Surveys, vol. 27:339-349 (1996).
Haddley, "MM-121," Human Anti-erbB-3 IgG2 MAb Oncolytic, Drugs of the Future, vol. 37(5):325-329 (2012).
Hamburger, Anne W. et al., "The Role of ErbB3 and its Binding Partners in Breast Cancer Progression and Resistance to Hormone and Tyrosine Kinase Directed Therapies," J. Mammary Gland Biol. Neoplasia, vol. 13(2):225-233 (2008).
Harms, Brian D. et al., "Application of computational modeling to guide the development of MM-111, a bispecific antibody targeting ErbB3 in ErbB2 overexpressing tumors," 2009 AACR Annual Meeting, Abstract No. 3298, 1 page (2009).
Harris, L.N et al., "Induction of sensitivity to doxorubicin and etoposide by transfection of MCF-7 breast cancer cells with heregulin beta-2," Clinical Cancer Research, 1998, vol. 4, pp. 1005-1012.
Harris, Lyndsay N. et al., "Molecular subtypes of breast cancer in relation to paclitaxel response and outcomes in women with metastatic disease: results from CALGB 9342," Breast Cancer Research, vol. 8(6):R66, 12 pages, doi:10.1186/bcr1622 (2006).
Heldin, Carl-Henrik, "Dimerization of Cell Surface Receptors in Signal Transduction," Cell, vol. 80:213-223 (1995).
Higgins, M. et al., "A Randomized, Double-Blind Phase II Trial of Exemestane+ MM-121, monoclonal antibody targeting ErbB3,or placebo in Postmenopausal Women with Locally Advanced or Metastatic ER+/PR+,Her2-negative Breast Cancer," American Society of Clinical Oncology, 2014, Poster Presentation, 1 page.
Holbro, Thomas et al., "The ErbB2/ErbB3 heterodimer functions as an oncogenic unit: ErbB2 requires ErbB3 to drive breast tumor cell proliferation," PNAS, vol. 100(15):8933-8938 (2003).
Holmes. F. et al., "A Randomized, Phase 2 Trial of Preoperative MM-121 with Paclitazel in triple Negative (TNBC) and Hormone Receptor (HR) Positive, HER2-negative Breast Cancer," San Antonio Breast Cancer Symposium—Dec. 9-13, 2014, Poster Presentation, 1 page.
Horan, Thomas et al., "Binding of Neu Differentiation Factor with the Extracellular Domain of Her2 and Her3," The Journal of Biological Chemistry, vol. 270(40):24604-24608 (1995).
Hsieh, AC et al., "Targeting HER proteins in cancer therapy and the role of the non-target HER3," British Journal of Cancer, vol. 97:453-457 (2007).
Htun Van Der Horst, Edward et al., "Anti-HER-3 MAbs Inhibit HER-3-Mediated Signaling in Breast Cancer Cell Lines Resistant to Anti-HER-2 Antibodies," Int. J. Cancer, vol. 115:519-527 (2005).
Huhalov, Alexandra et al., "MM-111: A novel ErbB3 antagonist with potent antitumor activity in ErbB2 over-expressing malignancies," 2009 MCR Annual Meeting, Abstract No. 5472, 2 pages (2009).
International Preliminary Report on Patentability and Written Opinion for Application No. PCT/US2011/028129, 8 pages, dated Sep. 11, 2012.
International Preliminary Report on Patentability and Written Opinion for Application No. PCT/US2012/042164, 8 pages, dated Mar. 25, 2014.
International Preliminary Report on Patentability for Application No. PCT/US2008/002119, dated May 18, 2009.
International Preliminary Report on Patentability for Application No. PCT/US2009/054051, dated Feb. 15, 2011.
International Preliminary Report on Patentability for Application No. PCT/US2012/028792, 15 pages, dated Sep. 17, 2013.

(56) References Cited

OTHER PUBLICATIONS

International Preliminary Report on Patentability, PCT/US2014/072594, dated Jun. 28, 2016, 7 pages.
International Search Report and Written Opinion for Application No. PCT/US2008/002119, dated Dec. 3, 2008.
International Search Report and Written Opinion for Application No. PCT/US2009/054051, dated May 4, 2010.
International Search Report and Written Opinion, International Application No. PCT/US2012/058871, dated Mar. 22, 2013 (11 paQes).
International Search Report and Written Opinion, PCT/US2014/072594, dated Jun. 29, 2015, 18 pages.
International Search Report and Written Opinion, PCT/US2016/027933, dated Jun. 24, 2016, 15 pages.
Peles, Elior et al., "Cell-type specific interaction of Neu differentiation factor (NDF/heregulin) with Neu/HER-2 suggests complex ligand-receptor relationships," The EMBO Journal, vol. 12(3):961-971 (1993).
Perez, E.,"Paclitaxel in breast cancer," The Oncologist, 3(6), pp. 373-389 (1998).
Petrelli, F. et al., "Current data of targeted therapies for the treatment of triple-negative advanced breast cancer: empiricism or evidence-based?" Expert Opin. Investig. Drugs, vol. 18(10) pp. 1467-1477 (2009).
Pierce, Jacalyn H. et al., "Signal Transduction Through the EGF Receptor Transfected in IL-3-Dependent Hematopoietic Cells," Science, vol. 239:628-631 (1988).
Pinkas-Kramarski, Ronit et al., "Diversification of Neu differentiation factor and epidermal growth factor signaling by combinatorial receptor interactions," The EMBO Journal, vol. 15(10):2452-2467 (1996).
Pinkas-Kramarski, Ronit et al., "Neu Differentiation Factor/Neuregulin Isoforms Activate Distinct Receptor Combinations," The Journal of Biological Chemistry, vol. 271(32):19029-19032 (1996).
Pinkas-Kramarski, Ronit et al., "The oncogenic ErbB-2/ErbB-3 heterodimer is a surrogate receptor of the epidermal growth factor and betacellulin," Oncogene, vol. 16:1249-1258 (1998).
Plowman, Gregory D. et al., "Heregulin induces tyrosine phosphorylation of HER4/p180erbB4," Nature, vol. 366:473-475 (1993).
Plowman, Gregory D. et al., "Ligand-specific activation of HER4/p180erbB4, a fourth member of the epidermal growth factor receptor family," Proc. Natl. Acad. Sci. USA, vol. 90:1746-1750 (1993).
Plowman, Gregory D. et al., "Molecular cloning and expression of an additional epidermal growth factor receptor-related gene," Proc. Natl. Acad. Sci. USA, vol. 87:4905-4909 (1990).
Poller, D.N. et al., "Production and Characterization of a Polyclonal Antibody to the c-erbB-3 Protein: Examination of c-erbB-3 Protein Expression in Adenocarcinomas," Journal of Pathology, vol. 168:275-280 (1992).
Prat, A. et al., "The role of hormonal therapy in the management of hormonal-receptor-positive breast cancer with co-expression of HER2," Nature Clinical Practice Oncology vol. 5(9), pp. 531-542 (2008).
Prigent, S.A. et al., "Expression of the c-erbB-3 protein in normal human adult and fetal tissues," Oncogene, vol. 7:1273-1278 (1992).
Prigent, Sally A. et al., "The Type 1 (EGFR-related) Family of Growth Factor Receptors and Their Ligands," Progress in Growth Factor Research, vol. 4:1-24 (1992).
Quinn, C.M. et al., "c-erbB-3 protein expression in human breast cancer: comparison with othe tumour variables and survival," Histopathology, vol. 25:247-252 (1994).
Rajkumar, T. et al., "A monoclonal antibody to the human c-erbB3 protein stimulates the anchorage-independent growth of breast cancer cell lines," Br. J. Cancer, vol. 70:459-465 (1994).
Rajkumar, T. et al., "Prevalence of c-erbB3 expression in squamous cell carcinomas of the cervix as determined by the monoclonal antibody RTJ2," International Journal of Oncology, vol. 6:105-109 (1995).
Rajkumar, Thangarajan et al., "Expression of the C-erbB-3 Protein in Gastrointestinal Tract Tumours Determined by Monoclonal Antibody RTJ1," Journal of Pathology, vol. 170:271-278 (1993).
Rajkumar, Thangarajan et al., "The Type I growth factor receptors in human breast cancer," Breast Cancer Research and Treatment, vol. 29:3-9 (1994).
Ritter, et al. "Human Breast Cancer Cells Selected for Resistance to Trastuzumab in vivo Overexpress Epidermal Growth Factor Receptor and ErbB Ligands and Remain Dependent on the ErbB Receptor; Network" Clinical Cancer Research, vol. 13, No. 16, Aug. 2007, pp. 4909-4919.
Ross, Jeffrey S. et al., "The HER-2/neu Oncogene in Breast Cancer: Prognostic Factor, Predictive Factor, and Target for Therapy," The Oncologist, vol. 3:237-252 (1998).
Rouzier, Roman et al., "Breast Cancer Molecular Subtypes Respond Differently to Preoperative Chemotherapy," Clin. Cancer Res., vol. 11(16):5678-5685 (2005).
Sadick, Michael D. et al., "Analysis of Heregulin-Induced ErbB2 Phosphorylation with a High-Throughput Kinase Receptor Activation Enzyme-Linked Immunosorbant Assay," Analytical Biochemistry, vol. 235:207-214 (1996).
Sak, M. et al., "Pertuzumab counteracts the inhibitory effect of ErbB2 on degradation of ErbB3," Carcinogenesis, vol. 34(9), pp. 2031-2038 (2013).
Salomon, David S. et al., "Epidermal growth factor-related peptides and their receptors in human malignancies," Critical Reviews in Oncology/Hematology, vol. 19:183-232 (1995).
Sanidas, E.E. et al., "Expression of the c-erbB-3 Gene Product in Gastric Cancer," Int. J. Cancer, vol. 54:935-940 (1993).
Sawyers, "The cancer biomarker problem," Nature, vol. 452, Apr. 2008, pp. 548-552.
Scartozzi, M. et al., "The Role of HER-3 Expression in the Prediction of Clinical Outcome for Advanced Colorectal Cancer Patients Receiving Irinotecan and Cetuximab," The Oncologist, vol. 16, pp. 53-60 (2011).
Schaefer, Karl-Ludwig et al., "Constitutive Activation of Neuregulin/ERBB3 Signaling Pathway in Clear Cell Sarcoma of Soft Tissue," Neoplasia, vol. 8(7):613-622 (2006).
Schaefer, Karl-Ludwig et al., "Expression Profiling of t(12;22) Positive Clear Cell Sarcoma of Soft Tissue Cell Lines Reveals Characteristic Up-Regulation of Potential New Marker Genes Including ERBB3," Cancer Research, vol. 64:3395-3405 (2004).
Schneider, Bryan P. et al., "Triple-Negative Breast Cancer: Risk Factors to Potential Targets," Clin. Cancer Res., vol. 14(24):8010-8018 (2008).
Schoeberl, B. et al., "Therapeutically targeting ErbB3: A key node in ligand-induced activation of the ErbB receptor-PI3K axis," Science Signaling, American Association for the Advancement of Science, vol. 2 (77), pp. 1-14 (2009).
Schoeberl, Birgit et al., "An ErbB3 Antibody, MM-121, Is Active in Cancers with Ligand-Dependent Activation," Cancer Res., vol. 70(6):2485-2494 (2010).
Schoeberl, Birgit et al., "Computational modeling and simulation lead to the development of MM-121, a human monoclonal antibody ErbB3 antagonist," 99th AACR Annual Meeting, Poster Presentation Abstract No. 1638 (2008).
Schoeberl, Birgit et al., "MM-121:a human monoclonal antibody ErbB3 antagonist," 99th AACR Annual Meeting, Poster Presentation Abstract No. 3974 (2008).
Semba, Kentaro et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, vol. 82:6497-6501 (1985).
Sequist, L. et al. "MM-121: A Human mAb to ErbB3," Santa Monica Lung Cancer Meeting, Presentation 14 pages, 2014.
Sequist, L.V. et al., "A Randomized Phase 2 Trial of MM-121, a Fully Human Monoclonal Antibody Targeting ErbB3, in Combination with Erlotinib, in EGFR Wild-type NSCLC Patients," American Society of Clinical Oncology, 2014, Poster Presentation, 1 page.
Sequist, L.V. et al., "Targeting EGFR and ERBB3 in Lung Cancer Patients: Clinical Outcomes in a Phase 1 Trial of MM-121 in Combination with Erlotinib," American Society of Clinical Oncology, 2012, Poster Presentation, 1 page.

(56) References Cited

OTHER PUBLICATIONS

Sequist, L.V. et al., "SHERLOC: A Phase 2 Study of Seribantumab (MM-121) in Combination with Docetaxel or Pemetrexed versus Docetaxel or Pemetrexed Alone in Patients with Heregulin Positive (HRG+), Locally Advanced or Metastatic Non-Small Cell Lung Cancer (NSCLC)," ASCO, Abstract No. TPS9110, 1 page (2009).
Sergina, et al. "Escape from HER-family tyrosine kinase inhibitor therapy by the kinase-inactive HER3" vol. 445, Nature, 2007, pp. 437-441.
Sheng et al., 'An activated ErbB3/NRG1 autocrine loop supports in vivo proliferation in ovarian; cancer cells.' Cancer Cell, Mar. 16, 2010 (Mar. 16, 2010), 17(3):298-310.
Skinner, Ann et al., "Transcriptional regulation of the c-erbB-3 gene in human breast carcinoma cell lines," Oncogene, vol. 8:3393-3401 (1993).
Shintani, Satoru et al., "Expression of C-erbB Family Gene Products in Adenoid Cystic Carcinoma of Salivary Glands: An Immunohistochemical Study," Anticancer Research, vol. 15:2623-2626 (1995).
Shintani, Satoru et al., "Prognostic significance of ERRB3 overexpression in oral squamous cell carcinoma," Cancer Letters, vol. 95:79-83 (1995).
Siddiqui, S. et al., "Pre-analytic variables and phospho-specific antibodies: the Achilles heel of immunohistochemistry," Breast Cancer Research, vol. 12(113, pp. 1-2, (2010).
Simpson, Barbara J.B. et al., "c-erbB Protein Expression in Ovarian Tumours," Int. J. Cancer (Pred. Oncol.), vol. 64:202-206 (1995).
Singer, Elizabeth et al., "Identification of a Heregulin Binding Site in HER3 Extracellular Domain," The Journal of Biological Chemistry, vol. 276(47):44266-44274 (2001).
Sithanandam et al., The ERBB3 receptor in cancer and cancer gene therapy, Cancer Gene Therapy, Jul. 2008 (Jul. 2008), Apr. 11, 2008 (Apr. 11, 2008)(ePub), 15:413-448.
U.S. Appl. No. 12/281,925, filed Sep. 5, 2008, Birgit Schoeberl.
U.S. Appl. No. 12/545,279, filed Aug. 21, 2009, Birgit Schoeberl.
U.S. Appl. No. 12/425,874, filed Apr. 17, 2009, Birgit Schoeberl.
U.S. Appl. No. 12/904,492, filed Oct. 14, 2010, Birgit Schoeberl.
U.S. Appl. No. 14/181,334, filed Feb. 14, 2014, Birgit Schoeberl.
U.S. Appl. No. 15/274,989, filed Sep. 23, 2016, Birgit Schoeberl.
U.S. Appl. No. 13/058,687, filed Feb. 11, 2011, Birgit Schoeberl.
U.S. Appl. No. 14/148,379, filed Jan. 6, 2014, Birgit Schoeberl.
U.S. Appl. No. 15/384,664, filed Dec. 20, 2016, Birgit Schoeberl.
U.S. Appl. No. 13/583,949, filed Sep. 11, 2012, Victor Moyo.
U.S. Appl. No. 14/518,900, filed Oct. 20, 2014, Victor Moyo.
U.S. Appl. No. 15/346,439, filed Nov. 8, 2016, Victor Moyo.
U.S. Appl. No. 14/004,598, filed Nov. 20, 2013, Gabriela Garcia.
U.S. Appl. No. 14/965,301, filed Dec. 10, 2015, Bambang Adiwijaya.
U.S. Appl. No. 15/156,262, filed May 16, 2016, Bambang Adiwijaya.
U.S. Appl. No. 15/386,723, filed Dec. 21, 2016, Bambang Adiwijaya.
U.S. Appl. No. 15/156,603, filed May 17, 2016, Bambang Adiwijaya.
U.S. Appl. No. 14/967,158, filed Dec. 11, 2015, Gavin MacBeath.
U.S. Appl. No. 12/281,925, Oct. 18, 2010, L. Bristol.
U.S. Appl. No. 12/281,925, Sep. 13, 2010, L. Bristol.
U.S. Appl. No. 12/281,925, Mar. 4, 2010, L. Bristol.
U.S. Appl. No. 12/545,279, Nov. 20, 2013, L. Bristol.
U.S. Appl. No. 12/545,279, Jun. 26, 2012, L. Bristol.
U.S. Appl. No. 12/545,279, Sep. 9, 2011, L. Bristol.
U.S. Appl. No. 12/545,279, May 20, 2011, L. Bristol.
U.S. Appl. No. 12/545,279, Feb. 17, 2011, L. Bristol.
U.S. Appl. No. 12/425,874, Apr. 14, 2010, L. Bristol.
U.S. Appl. No. 12/904,492, Oct. 15, 2014, L. Bristol.
U.S. Appl. No. 12/904,492, Jul. 24, 2014, L. Bristol.
U.S. Appl. No. 12/904,492, Feb. 20, 2014, L. Bristol.
U.S. Appl. No. 14/181,334, Jun. 22, 2016, L. Bristol.
U.S. Appl. No. 14/181,334, Feb. 19, 2016, L. Bristol.
U.S. Appl. No. 14/181,334, Oct. 27, 2015, L. Bristol.
U.S. Appl. No. 14/181,334, Jun. 25, 2015, L. Bristol.
U.S. Appl. No. 14/181,334, Mar. 6, 2015, L. Bristol.
U.S. Appl. No. 13/058,687, Sep. 5, 2013, L. Goddard.
U.S. Appl. No. 13/058,687, Jun. 27, 2013, L. Goddard.
U.S. Appl. No. 13/058,687, Feb. 5, 2013, L. Goddard.
U.S. Appl. No. 13/058,687, Nov. 7, 2012, L. Goddard.
U.S. Appl. No. 14/148,379, Jun. 20, 2016, L. Goddard.
U.S. Appl. No. 14/148,379, Aug. 5, 2015, L. Goddard.
U.S. Appl. No. 14/148,379, Jan. 7, 2015, L. Goddard.
U.S. Appl. No. 14/148,379, Sep. 12, 2014, L. Goddard.
U.S. Appl. No. 13/583,949, Jul. 23, 2014, J. Roark.
U.S. Appl. No. 13/583,949, Jan. 7, 2014, J. Roark.
U.S. Appl. No. 14/518,900, Aug. 9, 2016, J. Roark.
U.S. Appl. No. 14/518,900, Mar. 15, 2016, J. Roark.
U.S. Appl. No. 14/518,900, Oct. 16, 2015, J. Roark.
U.S. Appl. No. 14/004,598, Sep. 14, 2015, J. Wu.
U.S. Appl. No. 14/004,598, May 5, 2015, J. Wu.
U.S. Appl. No. 14/965,301, Feb. 23, 2017, N. Moseley.
U.S. Appl. No. 14/965,301, Aug. 4, 2016, N. Moseley.
U.S. Appl. No. 14/965,301, Mar. 28, 2016, N. Moseley.
U.S. Appl. No. 15/156,603, Dec. 28, 2016, M. Natarajan.
U.S. Appl. No. 14/967,158, Jan. 6, 2017, S. Rawlings.
Presta, Leonard, "Antibody engineering for therapeutics," Current Opinion in Structural Biology, vol. 13:519-525 (2003).
Reply dated Jan. 19, 2016, to Communication Pursuant to Article 94(3) including Reply to Third Party Observations in European Patent Application No. 12775896 (EP2764364) (5 pages).
Rudikoff, Stuart et al., "Single amino acid substitution altering antigen-binding specificity," Proc. Natl. Acad. Sci. USA, vol. 79:1979-1983 (1982).
Rudnick, Stephen I. et al., "Affinity and Avidity in Antibody-Based Tumor Targeting," Cancer Biotherapy and Radio pharmaceuticals, vol. 24(2):155-161 (2009).
Sabnis, G. et al., "Trastuzumab Reverses Letrozole Resistance and Amplifies the Sensitivity of Breast Cancer Cells to Estrogen," Cancer Research, vol. 69:1416-1428 (abstract) (2009).
Schmidt, M. et al., "Targeted inhibition of tumour cell growth by a bispecific single-chain toxin containing an antibody domain and TGFa," British Journal of Cancer, vol. 74:853-862 (1996).
Song, Mi-Kyung et al., "Light Chain of Natural Antibody Plays a Dominant Role in Protein Antigen Binding," Biochemical and Biophysical Research Communications, vol. 268:390-394 (2000).
Thurber, Greg M. et al., "Antibody tumor penetration: Transport opposed by systemic and antigen-mediated clearance," Advanced Drug Delivery Reviews, vol. 60:1421-1434 (2008).
Wainstein, Mark A. et al., "CWR22: Androgen-dependent Xenograft Model Derived from a Primary Human Prostatic Carcinoma," Cancer Research, vol. 54:6049-6052 (1994).
Ward, E. Sally et al., "Binding activities of a repertoire of single immunoglobulin variable domains secreted from *Escherichia coli*," Nature, vol. 341:544-546 (1989).
Wikipedia entry "Paclitaxel", English, accessed Aug. 13, 2015.
Yamamoto, Tadashi et al., "Similarity of protein encoded by the human c-erb-B-2 gene to epidermal growth factor receptor," Nature, vol. 319:230-234 (1986).
International Search Report for Application No. PCT/US2011/028129, 4 pages, dated Oct. 13, 2011.
International Search Report for Application No. PCT/US2012/028792, 7 pages, dated Nov. 7, 2012.
International Search Report issued in corresponding application No. PCT/US2014/058437 dated Apr. 13, 2015.
Issing, W.J. et al., "erbB-3, a third member of the erbB/epidermal growth factor receptor gene family: its expression in head and neck cancer cell lines," Eur. Arch. Otorhinolaryngol, vol. 250:392-395 (1993).
Jiang, N. et al., "Combined Treatment with HER3 Antibody MM-121/SAR 256212 and EGFR Antibody Cetuximab for Pre-clinical Models of Head and Neck Cancer," American Association for Cancer Research (AACR) Annual meeting 2013, Emory University Poster, 1 page.
Jones, Jennifer T. et al., "Binding specificities and affinities of egf domains for ErbB receptors," FEBS Letters, vol. 447:227-231 (1999).
Karunagaran, Devarajan et al., "ErbB-2 is a common auxiliary subunit of NDF and EGF receptors: implications for breast cancer," The EMBO Journal, vol. 15(2):254-264 (1996).

(56) References Cited

OTHER PUBLICATIONS

Kasprzyk, Philip G. et al., "Therapy of an Animal Model of Human Gastric Cancer Using a Combination of Anti-erbB-2 Monoclonal Antibodies," Cancer Research, vol. 52:2771-2776 (1992).
Katoh, Masaru et al., "c-erbB3 Gene Encodes Secreted as Well as Transmembrane Receptor Tyrosine Kinase," Biochemical and Biophysical Research Communications, vol. 192(3):1189-1197 (1993).
Kim, Hong-Hee et al., "Epidermal Growth Factor-dependent Association of Phosphatidylinositol 3-Kinase with the erbB3 Gene Product," The Journal of Biological Chemistry, vol. 269(40):24747-24755 (1994).
Kim, Hong-Hee et al., "Signal transduction by epidermal growth factor and heregulin via the kinase-deficient ErbB3 protein," Biochem. J., vol. 334:189-195 (1998).
Kita, Yoshiko A. et al., "NDF/heregulin stimulates the phosphorylation of Her3/erbB3," FEBS Letters, vol. 349:139-143 (1994).
Klapper, Leah N. et al., "A subclass of tumor-inhibitory monoclonal antibodies to ErbB-2/HER2 blocks crosstalk with growth factor receptors," Oncogene, vol. 14:2099-2109 (1997).
Konecny, GE et al., "Activity of the dual kinase inhibitor lapatinib (GW572016) against HER-2-overexpressing and trastuzumab-treated breast cancer cells," Cancer Research, vol. 66, p. 1630-1639 (2006).
Korabiowska, Monika et al., "Differential Expression of cerbB3 in Naevi and Malignant Melanomas," Anticancer Research, vol. 16:471-474 (1996).
Kraus, Matthias H. et al., "Demonstration of ligand-dependent signaling by the erbB-3 tyrosine kinase and its constitutive activation in human breast tumor cells," Proc. Natl. Acad. Sci. USA, vol. 90:290-2904 (1993).
Kraus, Matthias H. et al., "Isolation and characterization of ERBB3, a third member of the ERBB/epidermal growth factor receptor family: Evidence for overexpression in a subset of human mammary tumors," Proc. Natl. Acad. Sci. USA, vol. 86:9193-9197 (1989).
Kraus, Matthias H. et al., "Overexpression of the EGF receptor-related proto-oncogene erbB-2 in human mammary tumor cell lines by different molecular mechanisms," The EMBO Journal, vol. 6(3):605-610 (1987).
Kruser T J and Wheeler DI, 'Mechanisms of Resistance to HER Family Targeting Antibodies,' Exp; Cell Res, Apr. 15, 2010 (Apr. 15, 2010), Jan. 11, 2010 (Jan. 11, 2010)(ePub), 316(7):1083-100.
Lal, P. et al., "Correlation of HER-2 Status With Estrogen and Progesterone Receptors and Histologic Features in 3,655 Invasive Breast Carcinomas," American Journal of Clinical Pathology, vol. 123, pp. 541-546 (2005).
Lee, Hakjoo et al., "A Naturally Occurring Secreted Human ErbB3 Receptor Isoform Inhibits Heregulin-stimulated Activation of ErbB2, ErbB3, and ErbB4," Cancer Research, vol. 61:4467-4473 (2001).
Lee, Hakjoo et al., "Isolation and characterization of four alternate c-erbB3 transcripts expressed in ovarian carcinoma-derived cell lines and normal human tissues," Oncogene, vol. 6:3243-3252 (1998).
Lee-Hoeflich, Si Tuen et al., "A Central Role for HER3 in HER2-Amplified Breast Cancer: Implications for Targeted Therapy," Cancer Res., vol. 68(14):5878-5887 (2008).
Lemoine, Nicholas R. et al., "The erbB-3 Gene in Human Pancreatic Cancer," Journal of Pathology, vol. 168:269-273 (1992).
Lenz, H.J., "Management and Preparedness for Infusion and Hypersensitivity Reactions," The Oncologist, vol. 12, pp. 601-609, (2007).
Lewis, Gail D. et al., "Growth Regulation of Human Breast and Ovarian Tumor Cells by Heregulin: Evidence for the Requirement of ErbB2 as a Critical Component in Mediating Heregulin Responsiveness," Cancer Research, vol. 56:1457-1465 (1996).
Liu, B. et al., "Downregulation of erbB3 abrogates erbB2-mediated tamoxifen resistance in breast cancer cells," Int J Cancer, vol. 120, pp. 1874-1882 (2007).
Liu, Bolin et al., "Estrogenic Promotion of ErbB2 Tyrosine Kinase Activity in Mammary Tumor Cells Requires Activation of ErbB3 Signaling," Mol. Cancer Res., vol. 7(11):1882-1892 (2009).
Liu, J. et al., "A Phase 1 Study of the anti-ErbB3 antibody MM-121 in combination with weekly paclitaxel in patients with advanced gynecological and breast cancers," European Society for Medical Oncology Annual Congress, Vienna, Austria, Sep. 28 to Oct. 2, 2012, Poster Presentation, 1 page.
Liu, J. et al., "A Phase 2 Randomized Open Label Study of MM-121, a Fully Human Monoclonal Antibody Targeting ErbB3, in Combination with Weekly Paclitaxel, Versus Weekly Paclitaxel Alone, in Patients with Plantinum Resistant/Refractory Ovarian Cancers," American Society of Clinical Oncology, 2014, Poster Presentation, 1 page.
MacBeath, G. et al., A Meta-Analysis of Biomarkers in Three Randomized, Phase 2 Studies of MM-121, a Ligand-Blocking Anti-ErbB3 Antibody, in Patients with Ovarian, Lung and Breast Cancers, European Society for Medical Oncology (ESMO) Annual Meeting, 2014, Madrid Spain, Poster Presentation, 1 page.
Marte, Barbara M. et al., "Neu Differentiation Factor/Heregulin Modulates Growth and Differentiation of HC11 Mammary Epithelial Cells," Molecular Endocrinology, vol. 9:14-23 (1995).
Masson, K. et a., "The ErbB3-targeting antibody MM-121 (seribantumab) abrogates heregulin-driven resistance to multiple chemotherapies in preclinical models," European Association for Cancer Research (EACR) AACR Poster, Merrrimack Pharmaceuticals, 2015, 1 page.
Masson, K. et al., "A network biology screen reveals ligand-receptor pathway connections and resistance; mechanisms to RTK-directed therapies in cancer cells," AACR, Abstract 1199 1 page (2016).
Mathews, S. et al., "Identification of Heregulin (HRG) expression as a driver of a difficult-to-treat cancer phenotype and development of a companion diagnostic for the HRG-ErbB3 targeting drug seribantumab," AACR, Abstract No. A19, 1 page (2016).
McDonagh, Charlotte F. et al., "Antitumor Activity of a Novel Bispecific Antibody That Targets the ErbB2/ErbB3 Oncogenic Unit and Inhibits Heregulin-Induced Activation of ErbB3," Mol. Cancer Ther., vol. 11(3):582-593 (2012).
Moscosco, Lisa M. et al., "Synapse-Associated Expression of an Acetylcholine Receptor-Inducing Protein, ARIA/Heregulin, and its Putative Receptors, ErbB2 and ErbB3, in Developing Mammalian Muscle," Developmental Biology, vol. 172:158-169 (1995).
Musgrove, Elizabeth A. et al., "Biological determinants of endocrine resistance in breast cancer," Nature Reviews Cancer, vol. 9:631-643 (2009).
Myers, Russell B. et al., "Expression of p160erbB-3 and p185erbB-2 in Prostatic Intraepithelial Neoplasia and Prostatic Adenocarcinoma," Journal of the National Cancer Institute, vol. 86(15):1140-1145 (1994).
Naidu, R. et al., "Expression of c-erbB3 protein in primary breast carcinomas," British Journal of Cancer, vol. 78(10):1385-1390 (1998).
Neve, et al, "A collection of breast cancer cell lines for the study of functionally distinct cancer subtypes" Cancer Cell, vol. 10(6):515-527 (2000).
Nie, L. et al., "High ErbB4/ErbB3 Ratio Attenuates Efficacy of Anti-ErbB3 Therapy," Abstract No. 677, European Association for Cancer Research (EACR) ErbB4 Poster, Merrrimack Pharmaceuticals, 2015, 1 page.
Nie, Lin et al., "Efficacy of MM121 in ER+ and triple negative breast cancer studies," Proceedings of the American Association for Cancer Research, vol. 51:436, Poster Presentation No. 1806 (2010).
Notice of Opposition to a European Patent for Patent No. EP 2318548, 7 pages, dated Jul. 21, 2014.
Notice of Opposition, European Application No. EP11730112.7, dated Oct. 13, 2015, pp. 1-21.
Oikawa, Tetsuro et al., "Frequent Expression of Genes for Receptor Tyrosine Kinases and Their Ligands in Human Pancreatic Cancer Cells," International Journal of Pancreatology, vol. 18(1):15-23 (1995).
Onsum, M. et al., "Prediction of xenograft response to MM-121, an anti-ErbB3 inhibitor, using computational modeling and measurements of five biomarkers," American Association for Cancer Research (AACR) Annual meeting, 2010, Monsum Biomarkers Poster, Abstract No. 3756, 1 page.

(56) References Cited

OTHER PUBLICATIONS

Opponents Written SubmissionSummons to Attend Oral Proceedings,European Patent for Patent No. EP 2318548, 24 pages, dated Jan. 11, 2016.
Paul, Fundamental Immunology, 3rd Edition, 1993, pp. 292-295.
U.S. Appl. No. 15/938,361, filed Mar. 28, 2018, Gavin MacBeath.
U.S. Appl. No. 15/274,989, May 3, 2018, L. Bristol.
U.S. Appl. No. 15/384,664, Dec. 27, 2017, L. Goddard.
U.S. Appl. No. 15/346,439, Dec. 1, 2017, J. Roark.
U.S. Appl. No. 15/386,723, Apr. 17, 2018, N. Moseley.
U.S. Appl. No. 15/156,603, Feb. 6, 2018, M. Natarajan.
U.S. Appl. No. 15/601,955, May 18, 2018, N. Moseley.
Extended European Search Report European Application No. 17150566.2 , dated Jan. 18, 2018, 15 pages.
Htun Van Der Horst., E. PhD Thesis: "The role of ErbB3/HER3 in gliomas and breast cancer: Molecular mechanisms and potential role as therapeutic target", Mar. 21, 2002, 6 pages.
International Preliminary Report on Patentability, PCT/US2016/027933, dated Oct. 17, 2017, 8 pages.
Merrimack Pharmaceuticals' Phase 1 Research Supports MM-121 Potential for Investigation As Combination With Chemotherapy in Patients With Advanced Solid Tumors, Press Release, dated Jun. 4, 2013, 2 pages ( http://www.evaluategroup.com/Universal/View.aspx?type=Story&id=432757) retreived Jul. 6, 2017.
Normanno, N. et al, "Prognostic applications of gene expression signatures in breast cancer," Oncology, vol. 77 (Suppl 1):2-8 (2009).
Onitilo, A. et al., "Breast Cancer Subtypes Based on ER/PR and Her2 Expression: Comparison of Clinicopathologic Features and Survival," Clinical Medicine & Research, vol. 7(1/2): 4-13 (2009).
Partial European Search Report, European Application No. 17150566.2 , dated Oct. 4, 2017, 19 pages.
Perou, CM et al, "Molecular portraits of human breast tumours," Nature,vol. 406 (6797):747-752 (2000).
Sorlie, T., "Molecular portraits of breast cancer: tumour subtypes as distinct disease entities," European Journal of Cancer, vol. 40: 2667-2675 (2004).
Stancovski, I. et al., "Mechanistic aspects of the opposing effects of monoclonal antibodies to the ERBB2 receptor on tumor growth," PNAS, vol. 88 (19):8691-8695 (1991).

* cited by examiner

| # | Cell line name | parental/engineered | ErbB4 (molecules/cell) | ErbB3 (molecules/cell) | ratio ErbB4/ErbB3 | log2-fold stimulation by HRG | log2-fold inhibition by MM-121 |
|---|---|---|---|---|---|---|---|
| 1 | A549 | parental | 18 | 1110 | 0.016 | 1.79 | 1.74 |
| 2 | A549-E4#5 (high) | engineered | 4912 | 1110 | 4.4 | | 0.58 |
| 3 | A549-E4#14 (medium) | engineered | 2579 | 1110 | 2.3 | | 1.15 |
| 4 | A549-E4#17 (low) | engineered | 160 | 1110 | 0.14 | | 1.84 |
| 5 | CAMA1 | parental | 65000 | 63800 | 1.0 | 0.34 | 0.09 |
| 6 | CAMA1-shErbB4 | engineered | 5359 | 41879 | 0.13 | | 0.46 |
| 7 | CAMA1-siErbB4 | engineered | 9157 | 51898 | 0.18 | | 0.38 |
| 8 | H460 | parental | 21800 | 159 | 137.1 | 0.14 | 0.00 |
| 9 | HS22 | parental | 141000 | 3860 | 36.5 | 1.00 | 0.00 |
| 10 | HS22-E4KD#1141 | engineered | 44700 | 3780 | 11.8 | | -0.07 |
| 11 | HS22-E4KD#1407 | engineered | 125000 | 1710 | 73.1 | | -0.07 |
| 12 | HS22-E4KD#1408 | engineered | 154000 | 5170 | 29.8 | | -0.07 |
| 13 | HS22-E4KD#9836 | engineered | 16800 | 1690 | 9.9 | | 0.05 |
| 14 | HS22-Scr | engineered | 115000 | 2680 | 42.9 | | -0.05 |
| 15 | HCC-1428 | parental | 12500 | 49000 | 0.26 | 0.33 | 0.32 |
| 16 | IGROV1 | parental | 34400 | 6490 | 5.3 | 1.54 | 0.01 |
| 17 | IGROV1-E4KD | engineered | 4100 | 4400 | 0.93 | | 0.67 |
| 18 | IGROV1-Scr | engineered | 27200 | 6140 | 4.4 | | 0.17 |
| 19 | MCF7 | parental | 1870 | 10200 | 0.18 | 0.38 | 0.32 |
| 20 | OVCAR3 | parental | 54800 | 49300 | 1.1 | 0.56 | 0.77 |
| 21 | OVCAR4 | parental | 8440 | 27300 | 0.31 | 0.56 | 0.42 |
| 22 | OVCAR8 | parental | 89 | 62899 | 0.00142 | 1.54 | 1.09 |
| 23 | OVCAR8-ErbB4 #4 | engineered | 13801 | 77299 | 0.18 | | 0.87 |
| 24 | OVCAR8-ErbB4 #5 | engineered | 44367 | 13330 | 3.3 | | 0.12 |
| 25 | OVCAR8-ErbB4 #9 | engineered | 26292 | 82177 | 0.32 | | 0.41 |
| 26 | OVCAR8-ErbB4 JMa CYT1 | engineered | 195906 | 108524 | 1.8 | | 0.22 |
| 27 | OVCAR8-ErbB4 JMa CYT2 | engineered | 229245 | 88082 | 2.6 | | 0.06 |
| 28 | OVCAR8-GFP | engineered | 15.61 | 72145 | 0.00022 | | 0.92 |
| 29 | PC3 | parental | 1550 | 8800 | 0.18 | 0.45 | 0.36 |
| 30 | SKOV3 | parental | 3120 | 247 | 12.6 | 0.16 | 0.18 |
| 31 | T47D | parental | 2900 | 26200 | 0.11 | 0.83 | 0.40 |
| 32 | ZR75-1 | parental | 3460 | 10800 | 0.32 | 1.37 | 0.52 |

FIG. 8

BIOMARKERS FOR PREDICTING OUTCOMES OF CANCER THERAPY WITH ERBB3 INHIBITORS

RELATED APPLICATIONS

This application claims the benefit of U.S. Provisional Application Ser. No. 62/171,062, filed Jun. 4, 2015. The content of the aforementioned application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 21, 2016, is named MMJ-054_SL.txt and is 1,760 bytes in size.

FIELD

Provided are methods of treating a patient with cancer with targeted therapies.

BACKGROUND

ErbB3 is a member of the epidermal growth factor receptor (EGFR) family of transmembrane receptor tyrosine kinases (RTKs). Upon stimulation by its ligand, heregulin (HRG), ErbB3 heterodimerizes with another member of the ErbB family of RTKs, such as ErbB1 (EGFR), ErbB2 (HER2) or ErbB4. This heterodimerization initiates multiple signaling cascades leading to downstream effects including cell proliferation and survival. Co-expression of HRG and ErbB3 is found in many cancers and has been associated with decreased overall survival rates. Moreover, a growing body of evidence has shown that ErbB3 signaling causes decreased sensitivity (resistance) to both chemotherapeutic and targeted agents.

Seribantumab (previously MM-121 or Ab #6) is an experimental human monoclonal anti-ErbB3 IgG2; see, e.g., U.S. Pat. Nos. 7,846,440; 8,691,771; 8,895,001 and 8,961,966; U.S. Patent Publication Nos. 20110027291, 20140127238, 20140134170, and 20140248280, as well as international Publication Nos. WO/2015/100459, WO/2013/023043, WO/2013/138371, and WO/2012/103341. It is administered by intravenous infusion (e.g., over the course of one hour) and is supplied as a clear liquid solution in sterile, single-use vials containing 10.1 ml of seribantumab at a concentration of 25 mg/ml in an aqueous solution of 20 mM histidine, 150 mM sodium chloride, pH 6.5, to be stored at 2-8° C.

The significance of ErbB4 in cancer biology is poorly understood, especially given that ErbB4 is either up-regulated or down-regulated in different cancer types. Its correlation with clinical outcome is also conflicting, as reports indicate that ErbB4 is correlated with both favorable and poor prognoses. This conflicting role of ErbB4 might be due to its four structurally and functionally different isoforms that are derived from alternative splicing of the single ErbB4 gene. The "JMa" and "JMb" isoforms differ in the extracellular juxtamembrane (JM) domains, and the "CYT1" and "CYT2" isoforms differ in the intracellular cytoplasmic (CYT) domains. Data from both in vitro and in vivo experiments using ErbB4 isoform-specific overexpressing cell lines suggests that JMa is related to cell proliferation and migration, whereas JMb is related to cell growth inhibition and apoptosis. ErbB4 has been reported to be involved in the resistance mechanism of hormonal or RTK-targeted therapy, and was found to be mutated in 5% of NSCLC and 20% of metastatic melanoma, increasing the interest in ErbB4-targeted therapies.

Identifying and validating biomarkers is critical for targeted therapy. A certain number of clinical trials fail due to misidentification of the appropriate patient population. HRG has been identified as the most important biomarker to predict seribantumab efficacy, and seribantumab is effective in the treatment of HRG-driven tumors by inhibiting HRG binding to ErbB3, and thus inhibiting HRG-induced ErbB3 dimerization with other ErbB proteins. Data from ongoing phase II clinical trials also indicate that seribantumab is effective only in certain patient populations that express HRG (see, e.g., co-pending international Publication No. WO/2015/100459).

SUMMARY

HRG is not only a potent ligand for ErbB3; it is also a potent ligand of ErbB4, and the binding affinities of HRG to ErbB3 and ErbB4 are similar. ErbB4 is a fully functional receptor tyrosine kinase with an intact kinase domain and the capability to form homodimers or heterodimers upon ligand binding, and to mediate downstream signaling pathways.

It has now been discovered that when ErbB4 is present in a tumor in a level that is in excess to the level of ErbB3, ErbB3-targeted therapeutics (e.g., anti-ErbB3 antibodies) are less effective in treating the tumor than when ErbB3 is present at a level that is equal to or in excess to the level of ErbB4. In particular, while an ErbB4/ErbB3 ratio of 1.3 or greater indicates that ErbB3-targeted therapeutics will be less effective than a lower ratio, in accordance with this disclosure, a tumor ErbB4/ErbB3 ratio of $\geq 1.3$ indicates that treatment for the tumor (i.e., for the patient having the tumor) should not comprise administration of an ErbB3 inhibitor. The limiting case of this ErbB4 effect is where ErbB4 is present and ErbB3 is completely absent, i.e., ErbB4/ErbB3 ratio of $\infty$, in which case it is certain that ErbB3-inhibitory (or uniquely ErbB3-targeted) therapeutics will have no direct impact on the tumor and thus it is all but certain that they will be ineffective, and the treatment ordered for the patient should not comprise administration of an ErbB3 inhibitor.

Accordingly, disclosed herein are methods for a healthcare provider to select treatment for, and order the selected treatment of a patient for a malignant tumor, the method comprising the following actions by the healthcare provider:

I) determining whether the tumor is characterized as exhibiting HRG-encoding RNA expression at levels detectable by RNA in situ hybridization (RNA-ISH) or by RT-PCR, II) determining whether the tumor is characterized as comprising a high ErbB4/ErbB3 ratio of >1.3, and subsequent to I) and II), ordering treatment to be administered to the patient for the tumor, wherein, A) if it is determined that the tumor is characterized as not expressing RNA-ISH-detectable or RT-PCR detectable HRG-encoding RNA, then the treatment ordered for the patient does not comprise administration of an ErbB3 inhibitor; or B) if it is determined that the tumor is characterized as expressing RNA-ISH-detectable or RT-PCR detectable HRG-encoding RNA, and the tumor is also determined to have a high ErbB4/ErbB3 ratio of $\geq 1.3$, then the treatment ordered for the patient does not comprise administration of an ErbB3 inhibitor; or C) if it is determined that the tumor is characterized as expressing HRG, and the tumor is also determined to have a low ErbB4/ErbB3 ratio of <1.3, then the treatment ordered for the patient by the healthcare provider comprises administration of an ErbB3 inhibitor, and preferably, the patient is treated in accordance with the order.

In one embodiment, the determining actions of one or more or all of A) and B) and I) and II) are carried out by consulting the patient's medical record. In one embodiment, the characterizations of one or more or all of A) and B) and C) are results of one or more analyses of one or more tumor biopsies. In another embodiment, the ratio of ErbB4/ErbB3 is a low ratio and is equal to or less than 1.3. In one embodiment, the ErbB3 inhibitor comprises an anti-ErbB3 antibody. In another embodiment, the anti-ErbB3 antibody is seribantumab. In another embodiment, the ErbB3 inhibitor comprises an anti-heregulin antibody, a heregulin-binding ErbB3 receptor fragment, or an ErbB3 anti-sense nucleic acid molecule.

In one aspect, disclosed herein are methods in which a healthcare provider orders treatment of a patient for a malignant tumor, wherein the tumor is characterized 1) as overexpressing HRG, and 2) as not comprising a high ErbB4/ErbB3 ratio, the method comprising ordering treatment for the patient for the tumor, which treatment comprises administration of an ErbB3 inhibitor. In one embodiment, the tumor is non-small cell lung cancer (NSCLC), renal cell carcinoma (RCC), melanoma (e.g., cutaneous or intraocular malignant melanoma), colorectal cancer, serous ovarian carcinoma, liver cancer, bone cancer, pancreatic cancer, skin cancer, cancer of the head or neck, breast cancer, lung cancer, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), spinal axis tumor, glioma, pituitary adenoma, Kaposi's sarcoma, epidermoid cancer, squamous cell cancer, or mesothelioma.

In one embodiment, the tumor is a heregulin (HRG) positive tumor, and optionally the HRG positivity is determined by a HRG RNA-ISH assay or by RT-PCR assay.

In another aspect, disclosed herein are methods of treating a patient diagnosed with a heregulin positive (HRG+) solid tumor having a ratio of expressed ErbB4 to ErbB3 of less than 1.3, comprising administering a therapeutically effective amount of an anti-ErbB3 antibody to the patient. In one embodiment, the anti-ErbB3 antibody comprises CDRH1, CDRH2, and CDRH3 sequences comprising the amino acid sequences set forth in SEQ ID NO:1 (CDRH1), SEQ ID NO:2 (CDRH2), and SEQ ID NO:3 (CDRH3); and CDRL1, CDRL2, and CDRL3 sequences comprising the amino acid sequences set forth in SEQ ID NO:4 (CDRL1), SEQ ID NO:5 (CDRL2), and SEQ ID NO:6 (CDRL3). In another embodiment, the expressed ErbB4 and ErbB3 are each detected by RNA in situ hybridization (RNA-ISH) or by RT-PCR. In another embodiment, the anti-ErbB3 antibody is seribantumab. In another embodiment, the tumor is a non-small cell lung cancer (NSCLC), renal cell carcinoma (RCC), melanoma (e.g., cutaneous or intraocular malignant melanoma), colorectal cancer, serous ovarian carcinoma, liver cancer, bone cancer, pancreatic cancer, skin cancer, cancer of the head or neck, breast cancer, lung cancer, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), spinal axis tumor, glioma, pituitary adenoma, Kaposi's sarcoma, epidermoid cancer, squamous cell cancer, or mesothelioma.

In another embodiment, the tumor is a HRG+, ER+, PR+, and HER2 negative breast cancer. In another embodiment, the tumor is platinum-resistant or refractory.

In another aspect, disclosed herein are antibody compositions for treating a malignant tumor in a human patient, the compositions comprising an antibody comprising CDRH1, CDRH2, and CDRH3 sequences comprising the amino acid sequences set forth in SEQ ID NO:1 (CDRH1), SEQ ID NO:2 (CDRH2), and SEQ ID NO:3 (CDRH3); and CDRL1, CDRL2, and CDRL3 sequences comprising the amino acid sequences set forth in SEQ ID NO:4 (CDRL1), SEQ ID NO:5 (CDRL2), and SEQ ID NO:6 (CDRL3), wherein the malignant tumor is a) HRG-positive and b) does not have a high ErbB4/ErbB3 ratio. In one embodiment, the ratio of ErbB4/ErbB3 is equal to or less than 1.3/1. In one embodiment, the ErbB3 inhibitor is an anti-ErbB3 antibody, optionally seribantumab. In another embodiment, the ErbB3 inhibitor comprises an anti-heregulin antibody, a heregulin-binding ErbB3 receptor fragment, or an ErbB3 anti-sense nucleic acid molecule. Optionally the tumor is a non-small cell lung cancer (NSCLC), renal cell carcinoma (RCC), melanoma (e.g., cutaneous or intraocular malignant melanoma), colorectal cancer, serous ovarian carcinoma, liver cancer, bone cancer, pancreatic cancer, skin cancer, cancer of the head or neck, breast cancer, lung cancer, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), spinal axis tumor, glioma, pituitary adenoma, Kaposi's sarcoma, epidermoid cancer, squamous cell cancer, or mesothelioma.

BRIEF DESCRIPTION OF THE DRAWINGS

FIG. 2A is a list of cell lines with the ErbB4/ErbB3 ratio and percent inhibition by seribantumab indicated. Twenty percent growth inhibition by seribantumab (as compared to control) was used as the cutoff to separate "responder" cell lines from "non-responder" cell lines. The results are expressed as mean+/-SD of triplicate wells. FIG. 2B shows examples of two responder cell lines, OVCAR-8 (ovarian) and A549 (lung) with low ErbB4/ErbB3 ratios. FIG. 2C shows examples of two non-responder cell lines with high ErbB4/ErbB3 ratios, IGR-OV1 (ovarian) and H522 (lung). FIG. 2D is a graph showing the correlation of HRG-stimulated cell growth with the ErbB4/ErbB3 ratio, and FIG. 2E shows the correlation of seribantumab-induced inhibition with the ErbB4/ErbB3 ratio.

FIG. 4A shows western blot analysis of extracts from transduced IGR-OV1 cells to confirm knockdown of ErbB4 by shErbB4, and shows the other ErbB members to demonstrate specificity. FIG. 4B shows the effect of seribantumab activity on HRG-induced signaling in cells transduced with shSCR or shErbB4, as analyzed by western blot. FIG. 4C shows the relative cell viability of wild type IGR-OV1 cells ("parental," left panel), cells transduced with either shSCR control (middle panel), or shErbB4 (right panel), and shows the effect of seribantumab on HRG-induced growth as tested by the CellTiter-Glo® (CTG) assay.

FIG. 5A is an image of a western blot showing ErbB4 and ErbB3 levels to confirm ErbB4 overexpression (and GADPH levels as a control). FIG. 5B is an image of a western blot of cells transduced with GFP control, ErbB4 JMaCYT1 or ErbB4 JMaCYT2 in order to test the effect of seribantumab activity on HRG-induced signaling in cells overexpressing these isoforms of ErbB4. FIG. 5C shows the relative cell viability of OVCAR-8 cells transduced with the GFP control ("GFP," left panel), ErbB4-JMaCYT1 (middle panel), or ErbB4-JMaCYT2 (right panel), and shows the effect of seribantumab on HRG-induced growth in cells overexpressing ErbB4, as tested by the CTG assay. FIG. 5D is an image of a western blot showing ErbB4 expression in individual selected clones of OVCAR-8 cells infected with lentivirus encoding ErbB4-JMaCYT1. FIG. 5E is an image of a western blot showing ErbB4 and ErbB3 levels for select clones. FIG. 5F is an image of a western blot showing the effect of seribantumab activity on HRG-induced cell signaling in select clones. FIG. 5G shows the effect of seribantumab on HRG-induced cell growth as tested by CellTiter-Glo® (CTG) assay.

FIG. 6A is a western blot showing ErbB4 and ErbB3 levels in ErbB4 siRNA and scrambled sequence siRNA transfected cells. FIG. 6B is a western blot showing the effect of seribantumab on HRG signaling in OVCAR-8-GFP control cells and ErbB4 over-expressing OVCAR-8 cells transfected with scrambled sequence siRNA or ErbB4siRNA. FIG. 6C shows the effect of seribantumab on HRG-induced cell growth tested by the CTG viability assay (HRG: 10 nM, seribantumab: 1250 nM).

FIG. 8 is a table showing collected data from the Examples. In the two right-hand columns, "stimulation" and "inhibition" refer to effects on cell proliferation. In the second column, parental/engineered refers to the nature of the cell line named in the same row in the first column.

DETAILED DESCRIPTION

Figure 1:
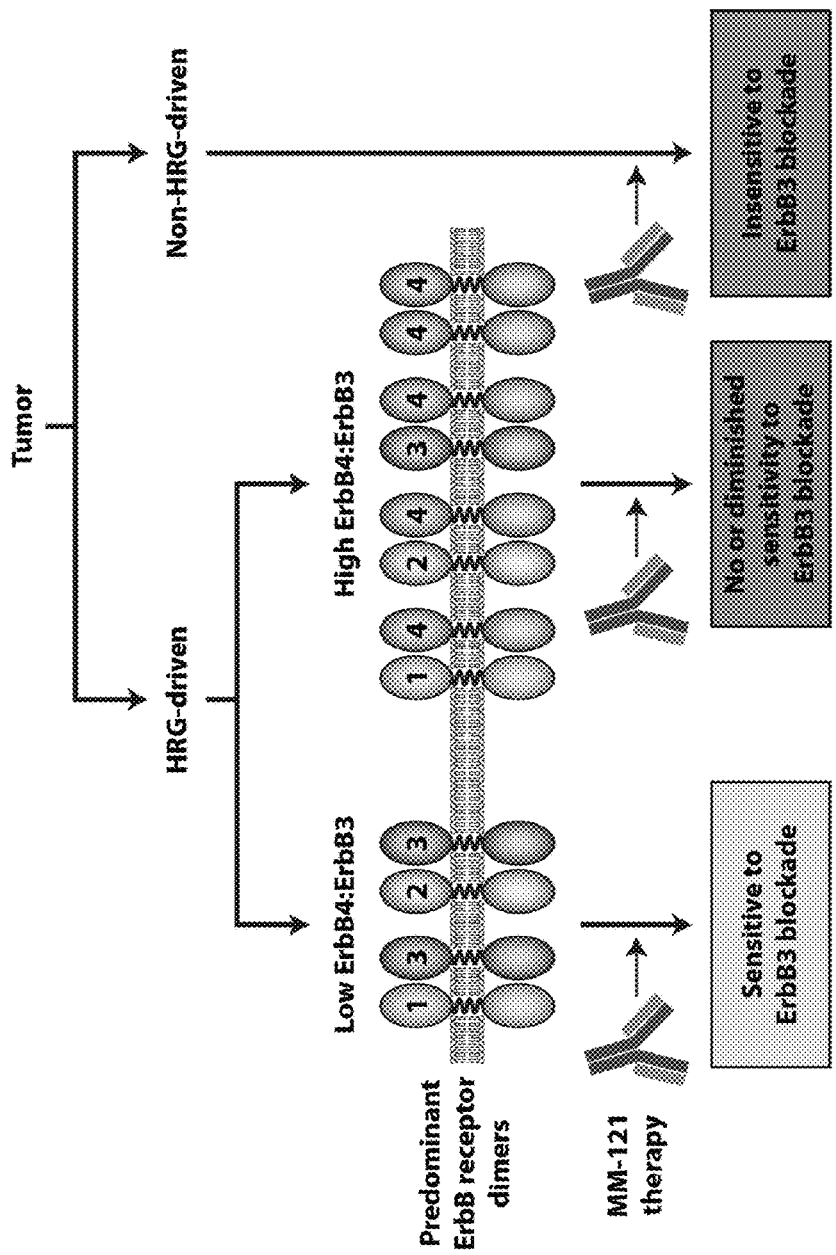
FIG. 1 is a schematic of the signaling hypothesis disclosed herein. Seribantumab is a human monoclonal ErbB3 antibody that competes with HRG for binding to ErbB3. Seribantumab inhibits the effect of HRG only in tumors with low ErbB4/ErbB3 ratio, indicating that a high ErbB4/ErbB3 ratio might interfere with seribantumab efficacy.

Provided herein are methods for selecting and/or optimizing therapy for patients having cancer (e.g., non-hematological cancers) by determining whether the patient will benefit from treatment with an ErbB3 inhibitor (e.g., an antibody, such as seribantumab), based on particular biomarker scores obtained from a biological sample of the patient (i.e., ErbB3 and ErbB4, and the ratio of ErbB4: ErbB3 (also denoted herein as "ErbB4/ErbB3")).

"ErbB3" and "HER3" both refer to human ErbB3 protein, as described in U.S. Pat. No. 5,480,968.

"ErbB3 inhibitor" indicates a therapeutic agent that inhibits, downmodulates, suppresses or downregulates activity or expression of ErbB3, e.g., an agent that does one or more of the following: reduces cellular ErbB3 levels, reduces ligand binding to ErbB3, and reduces ErbB3-mediated intracellular signal transduction. The term is intended to include small molecule kinase inhibitors, antibodies, interfering RNAs (shRNA, siRNA), soluble receptors, and the like. Exemplary ErbB3 inhibitors are an anti-ErbB3 antibody, an anti-heregulin antibody, a heregulin-binding ErbB3 receptor fragment, or an ErbB3 anti-sense nucleic acid molecule. Representative inhibitors of ErbB3 and HRG binding and methods of their use are disclosed, e.g., in U.S. Pat. Nos. 7,125,680 and 7,314,916.

An "anti-ErbB3 antibody" is an antibody that immunospecifically binds to the ectodomain of ErbB3. The antibody may be an isolated antibody. Exemplary anti-ErbB3 antibodies inhibit ligand-mediated phosphorylation of ErbB3 by HRG, and some (such as seribantumab) also inhibit phosphorylation of ErbB3 mediated by one or more of the EGF-like ligands EGF, TGFα, betacellulin, heparin-binding epidermal growth factor, biregulin, epigen, epiregulin, and amphiregulin.

An "antibody," is a protein consisting of one or more polypeptides comprising binding domains substantially encoded by immunoglobulin genes or fragments of immunoglobulin genes, wherein the protein immunospecifically binds to an antigen. One type of naturally occurring immunoglobulin structural unit (e.g., an IgG) comprises a tetramer that is composed of two identical pairs of polypeptide chains, each pair having one "light" (about 25 kD) and one "heavy" chain (about 50-70 kD). "VL" and VH" refer to the variable regions of these light and heavy chains respectively. "Antibodies" include intact proteins as well as antigen-binding fragments, which may be produced by digestion of intact proteins, e.g., with various peptidases, or may be synthesized de novo either chemically or using recombinant DNA expression technology. Such fragments include, for example, F(ab)2 dimers and Fab monomers, and single chain antibodies. Single chain antibodies exist, generally due to genetic engineering, as a single polypeptide chain, e.g., single chain Fv antibodies (scFv) in which a VH fragment and a VL fragment are joined together (directly or through a peptide linker) to form a continuous polypeptide that retains immunospecific binding activity. Inhibitors can inhibit growth of such tumors.

The terms "suppress", "suppression", "inhibit" and "inhibition" as used herein, refer to any statistically significant decrease in biological activity (e.g., tumor cell growth), including full blocking of the activity. For example, "inhibition" can refer to a decrease of about 10%, 20%, 30%, 40%, 50%, 60%, 70%, 80%, 90%, or 100% in biological activity.

The term "patient" indicates a human subject receiving either prophylactic or therapeutic treatment.

The terms "treat," "treating," and "treatment," as used herein, refer to therapeutic or preventative (prophylactic) measures such as those described herein. The methods of "treatment" employ administration to a patient of an ErbB3 inhibitor as provided herein, for example, a patient having cancer, in order to prevent, cure, delay, reduce the severity of, or ameliorate one or more symptoms of the cancer, or in order to prolong the survival of a patient beyond that expected in the absence of such treatment.

The term "effective amount," as used herein, refers to that amount of an agent, such as an anti-ErbB3 antibody, which is sufficient to product a therapeutic benefit when administered to a patient.

The terms "anti-cancer agent" and "antineoplastic agent" refer to drugs used to treat malignancies, such as cancerous growths.

ErbB3 Inhibitors

Methods provided herein can be used to predict efficacy of therapeutic treatment using any suitable ErbB3 inhibitor or combination of inhibitors.

In one embodiment, the ErbB3 inhibitor is an anti-ErbB3 antibody, e.g., a monoclonal antibody. In an exemplary embodiment, the ErbB3 inhibitor is seribantumab. Alternately, the anti-ErbB3 monoclonal antibody is an antibody that competes with seribantumab for binding to ErbB3. In another embodiment, the anti-ErbB3 antibody is an antibody comprising the $V_H$ and $V_L$ CDR sequences of seribantumab in the same relative order as they are present in seribantumab, and which are disclosed herein as SEQ ID NOs: 1-3 ($V_H$ CDR1, 2, 3) and 4-6 ($V_L$ CDR1, 2, 3), respectively. Other examples of anti-ErbB3 antibodies include Ab #3, Ab #14, Ab #17 and Ab #19, also described further in WO 2008/100624 and U.S. Pat. No. 7,846,440, and having $V_H$ and $V_L$ sequences as disclosed in the patent as SEQ ID NOs: 9 and 10, 17 and 18, 25 and 26, and 33 and 34, respectively. In another embodiment, the anti-ErbB3 antibody is an antibody comprising the $V_H$ and $V_L$ CDR sequences of Ab #3 (shown in the patent as SEQ ID NOs: 11-13 and 14-18, respectively) or antibody comprising the $V_H$ and $V_L$ CDR sequences of Ab #14 (shown in SEQ ID NOs: 19-21 and 22-24, respectively) or an antibody comprising the $V_H$ and $V_L$ CDR sequences of Ab #17 (shown in the patent as SEQ ID NOs: 27-29 and 30-32, respectively) or an antibody comprising the $V_H$ and $V_L$ CDR sequences of Ab #19 (shown in the patent as SEQ ID NOs: 35-37 and 38-40, respectively), each of said CDRs being present in the same relative order as they are present in the corresponding Ab # antibody.

Yet other anti-ErbB3 binding sites (or portions thereof, such as CDRs, V domains or chains) that may be used are those from the anti-ErbB3 antibodies 1B4C3 (cat # sc-23865, Santa Cruz Biotechnology) and 2D1D12 (U3 Pharma AG), both of which are described in, e.g., U.S. Pat. No. 9,011,851, and are produced by hybridoma cell lines DSM ACC 2527 or DSM ACC 2517 (deposited at DSMZ); AV-203 (SEQ ID NO:190 (heavy chain) and SEQ ID NO:206 (light chain) in U.S. Pat. No. 8,481,687 (Aveo Pharmaceuticals); 8B8 (produced by ATCC® hybridoma #HB-12070™ and described in WO 1997/035885, Genentech); the monoclonal antibody mAb 205.10.2 (SEQ ID NO:8 (heavy chain) and SEQ ID NO:10 (light chain) in U.S. Pat. No. 8,859,737, Roche Glycart); the murine anti-ErbB3 antibody described in U.S. Pat. No. 8,362,215 (Trellis Biosciences) or the bispecific anti-ErbB3/anti-EGFR antibody MEHD7945a, Genentech).

Patient Populations

Provided herein are effective methods for treating cancer in a human patient and for selecting patients to be so treated. In one embodiment, the human patient suffers from a cancer selected from the group consisting of non-small cell lung cancer (NSCLC), renal cell carcinoma (RCC), melanoma (e.g., cutaneous or intraocular malignant melanoma), colorectal cancer, serous ovarian carcinoma, liver cancer, bone cancer, pancreatic cancer, skin cancer, cancer of the head or neck, breast cancer, lung cancer, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), spinal axis tumor, glioma, pituitary adenoma, Kaposi's sarcoma, epidermoid cancer, squamous cell cancer, and mesothelioma. The disclosed methods are also applicable to treatment of metastatic cancers. In a particular embodiment, the cancer is ovarian cancer. In another particular embodiment, the cancer is breast cancer. The breast cancer may be either or both of ER+ and PR+ breast cancer ("ER+ and/or PR+"). The breast cancer may be HER2 negative. The breast cancer may be either or both of 1) ER+ and/or PR+ and 2) HER2 negative. Methods for testing ER and PR status are used as a matter of clinical routine in the treatment of gynecological tumors. Such methods may be carried out in accordance with the well-established guidelines of Hammond, M E et al., "American Society of Clinical Oncology/College of American Pathologists Guideline Recommendations for Immunological Testing of Estrogen and Progesterone Receptors in Breast Cancer" *Arch Pathol Lab Med.* 2010; 134:E1-E16. HER2 status may be determined using HCT, with a score of 3+ being considered HER2 positive and a score of 2+ or 1+ or 0 being considered HER2 negative.

In one embodiment, a human patient for treatment using the subject methods and compositions has evidence of recurrent or persistent disease following primary chemotherapy.

In another embodiment, a human patient for treatment using the subject methods and compositions has had at least one prior platinum based chemotherapy regimen for management of primary or recurrent disease.

In another embodiment, the patient has a cancer that is platinum-resistant or refractory. In one example, the platinum-resistant cancer is ovarian cancer.

In another embodiment, a human patient for treatment using the subject methods and compositions has evidence of recurrent or persistent disease following a) primary treatment, e.g., with an anti-estrogen therapy or b) an adjuvant treatment with a non-steroidal aromatase inhibitor and/or tamoxifen.

In another embodiment, the cancer undergoing treatment is advanced. In one aspect, the term "advanced" cancer denotes a cancer above Stage II. In another, "advanced" refers to a stage of disease where chemotherapy is typically recommended, which is any one of the following: 1) in the setting of recurrent disease: any stage or grade; 2) stage IC or higher, any grade; 3) stage IA or IB, grade 2 or 3; or 4) in the setting of incomplete surgery or suspected residual disease after surgery (where further surgery cannot be performed): any stage or grade.

Outcomes

The efficacy of the treatment methods provided herein can be assessed using any suitable means. In one embodiment, the treatment produces at least one therapeutic effect selected from the group consisting of reduction in growth rate of tumor, reduction in size of tumor, reduction in number of metastatic lesions over time, increase in duration of progression-free survival, and increase in overall response rate.

With respect to target lesions, responses to therapy may include:

Complete Response (CR):

Disappearance of all target lesions. Any pathological lymph nodes (whether target or non-target) must have reduction in short axis to <10 mm;

Partial Response (PR):

At least a 30% decrease in the sum of the diameters of target lesions, taking as reference the baseline sum diameters;

Progressive Disease (PD):

At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression); and Stable Disease (SD):

Neither sufficient shrinkage to qualify for PR, nor sufficient increase to qualify for PD, taking as reference the smallest sum diameters while on study. (Note: a change of 20% or less that does not increase the sum of the diameters by 5 mm or more is coded as stable disease). To be assigned a status of stable disease, measurements must have met the stable disease criteria at least once after study entry at a minimum interval of 6 weeks.

With respect to non-target lesions, responses to therapy may include:

Complete Response (CR):

Disappearance of all non-target lesions and normalization of tumor marker level. All lymph nodes must be non-pathological in size (<10 mm short axis). If tumor markers are initially above the upper normal limit, they must normalize for a patient to be considered in complete clinical response;

Non-CR/Non-PD:

Persistence of one or more non-target lesion(s) and/or maintenance of tumor marker level above the normal limits; and Progressive Disease (PD):

Appearance of one or more new lesions and/or unequivocal progression of existing non-target lesions. Unequivocal progression should not normally trump target lesion status. It must be representative of overall disease status change, not a single lesion increase.

In exemplary outcomes, patients treated according to the methods disclosed herein may experience improvement in at least one sign of a cancer, such as platinum resistant/refractory advanced ovarian cancer.

In one embodiment, the patient so treated exhibits CR, PR, or SD.

In another embodiment, the patient so treated experiences tumor shrinkage and/or decrease in growth rate, i.e., suppression of tumor growth. In yet another embodiment, one or more of the following can occur: the number of cancer cells is reduced; tumor size is reduced; cancer cell infiltration into peripheral organs is inhibited, retarded, slowed, or stopped; tumor metastasis is slowed or inhibited; tumor growth is inhibited; recurrence of tumor is prevented or delayed; or one or more of the symptoms associated with cancer is relieved to some extent.

In other embodiments, such improvement is measured by a reduction in the quantity and/or size of measurable tumor lesions. Measurable lesions are defined as those that can be accurately measured in at least one dimension (longest diameter is to be recorded) as >10 mm by either or both of CT scan (CT scan slice thickness no greater than 5 mm) and caliper measurement via clinical exam, or as >20 mm by chest X-ray. The size of non-target lesions, e.g., pathological lymph nodes, can also be measured for improvement. In one embodiment, lesions can be measured on chest x-rays or CT or MRI outputs.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

The following Examples are illustrative and should not be construed as limiting the scope of this disclosure in any way, as many variations and equivalents will become apparent to those skilled in the art upon reading the present disclosure.

EXAMPLES

Materials and Methods

Materials

The ErbB4 shRNA lentivirus is from Sigma-Aldrich® (St. Louis, Mo., USA; cat # TRCN00000014011). The ErbB4 JMaCYT1 and ErbB4 JMaCYT2 isoform cDNA lentivirus (Catalog Nos. LP-A0212-Lv105 and LP-Z4265-Lv105, respectively) are from GeneCopoeia™ (Rockville, Md., USA). The 3D NanoCulture™ plates are from SCIVAX Life Sciences, Inc. (Woburn, Mass., USA). All materials for western blot assays are from Bio-Rad Laboratories (Hercules, Calif., USA). Antibodies against pErbB3, pAkt, pERK, total EGFR and ErbB4 are from Cell Signaling Technology® (Beverly, Mass., USA; cat #s 4561, 9271, 4370, 2232, and 4795, respectively). The antibody against total ErbB3 is from Abcam® (Cambridge, Mass., USA; cat #1186-1). The antibodies against GAPDH (cat#MAB374) and total ErbB2 (cat#04-291) are from EMD Millipore (Temecula, Calif., USA). The secondary antibodies are from Li-Cor® Biosciences (Lincoln, Nebr., USA; IRDye® 680 anti-mouse IgG: #926-32222 and IRDye® 800 anti-rabbit IgG: #926-32211). HRG1-beta 1 is from R&D Systems™ (Minneapolis, Minn., USA; cat#396-HB). CellTiter-Glo® Luminescent Cell Viability Assay kit is from Promega (Madison, Wis., USA). ErbB4 siRNA (cat# L-003128-00), scrambled sequence siRNA (cat# D-001310-01) and transfection reagent (Dharmafect®, cat# T-2001-01) are purchased from Dharmacon, Inc. (Lafayette, Colo., USA). Cell culture medium and all other reagents are from Gibco®/Life Technologies unless otherwise specified.

Cell Culture

Cell lines from NCI-60 panel (NCI, Rockville, Md., USA) are cultured in RPMI 1640 (ATCC® 30-2001™) supplemented with 10% fatal calf serum (FCS), 2 mM of L-glutamine, and 100 units/ml penicillin/streptomycin. ErbB4-engineered cell lines are cultured in above medium plus puromycin to maintain their genotype. All cells are grown in a humidified atmosphere at 37° C. with 5% $CO_2$, unless otherwise indicated. Cells are sub-cultured every 3-4 days to maintain a logarithmic growth phase. Cell lines from the NCI-60 anti-cancer cell lines used in the assays disclosed herein include, e.g., those in FIG. 2A. FIG. 8 is a summary of all parental and engineered cell lines used in the Examples below.

Cell Viability/Proliferation Assay

Cells are sub-cultured one day before to make sure they are in log growing phase. Cells are then seeded either into 96-well 3D NanoCulture™ plate at a density of 5000 cells/well or into 96-well 2D culture plate at a density of 800-2000 cells/well depending on cell growth rate and cultured in RPMI containing 2% fetal calf serum for 24 hr. The cells are then treated with different doses of seribantumab in the presence or absence of 10 nM HRG, each dose is in triplicates. At day 5, cell viability is measured using the CTG assay according to the manufacturer's instructions. Results are expressed as mean+/−SEMD of triplicate wells.

In Vivo Efficacy Study

Female nu/nu nude mice (NU-Foxn1nu, Charles River Laboratories, Wilmington, Mass., USA), 4-5 weeks of age, weighing 16±0.5 g, are inoculated with 0.2 ml of cell suspension in phosphate buffered saline (PBS): Growth Factor Reduced Matrigel® (BD Biosciences) of IGR-OV1 ($8*10^6$/mouse) or A549 ($5*10^6$/mouse), or OVCAR-8 ($8*10^6$/mouse). Each tumor model is represented by a parental control, green fluorescent protein, or scrambled sequence control and ErbB4 modified versions. Once tumors reached approximately 200 $mm^3$ in volume, the mice are randomized into treatment groups (10 mice/group) to receive either 600 µg seribantumab or PBS (control) every 3 days (Q3D). Tumor dimensions are measured twice a week and the tumor volumes calculated using the formula: $\pi/6 \times L \times W2$, where L and W, respectively, represented the larger and smaller tumor diameter. At the end of the four week treatment, mice are sacrificed and tumor bulk collected and frozen.

Stable transduction of target cells with lentiviruses—Stable ErbB4 knockdown or over-expression engineered cell lines are established by transducing either ErbB4 shRNA lentivirus or ErbB4 JMaCYT1 and JMaCYT2 isoform lentivirus into proper cell lines. Cells are seeded into 24-well plates and cultured in complete medium overnight. At 70-80% confluence, transduce the cells by removing the old medium and replacing it with 0.5 ml of complete medium (without antibiotics) containing 8 µg/ml of Polybrene® and diluted lentivirus. Culture the transduced cells in a standard 37C cell culture incubator overnight. Replace the virus containing old medium with fresh complete culture medium and culture it overnight. Two days after the transduction, subculture the cells into 10-cm petri-dish with complete medium containing the different concentrations of selection antibiotics determined by kill curve of each target cell lines. The selection medium is changed every 3-4 days. The ErbB4 knockdown or over-expression in the selection drug resistant pooled cells are validated by western blotting.

Western Blotting

Cells are seeded into 6-well culture plates at 70% confluence and cultured in RPMI containing 10% FBS overnight. The medium is changed to 2% FBS medium and cells are pre-incubated with 250 nM of seribantumab, or buffer (control), for 1 hr. The cells are then stimulated with HRG-1-beta-1 EGF domain at a final concentration of 10 nM for 10 minutes. The reaction is stopped by removing the supernatants and washing with ice-cold PBS. The cells are harvested in 2× protein sample buffer by scraping the cells. The genomic DNA is sheared by passing it through a 21-gauge syringe needle several times. The homogenized cell lysates are boiled for 5 min and centrifuged at 12,000 rpm for 5 min. Protein from $5*10^4$ cells (25 µg) is subjected to electrophoresis on 4-12% gradient gels and electro-transferred to nitrocellulose membrane (BioRad). Nonspecific binding is blocked by incubating with blocking buffer (#927-40000, LI-COR®). Western blots of the gels are probed with different primary antibodies (Cell Signaling, see materials above) followed by incubating with secondary antibody (LI-COR). The blots are then imaged on a LI-COR Odyssey® infra-red imaging system. GAPDH is detected in each blot as an internal control.

Figure 2A:
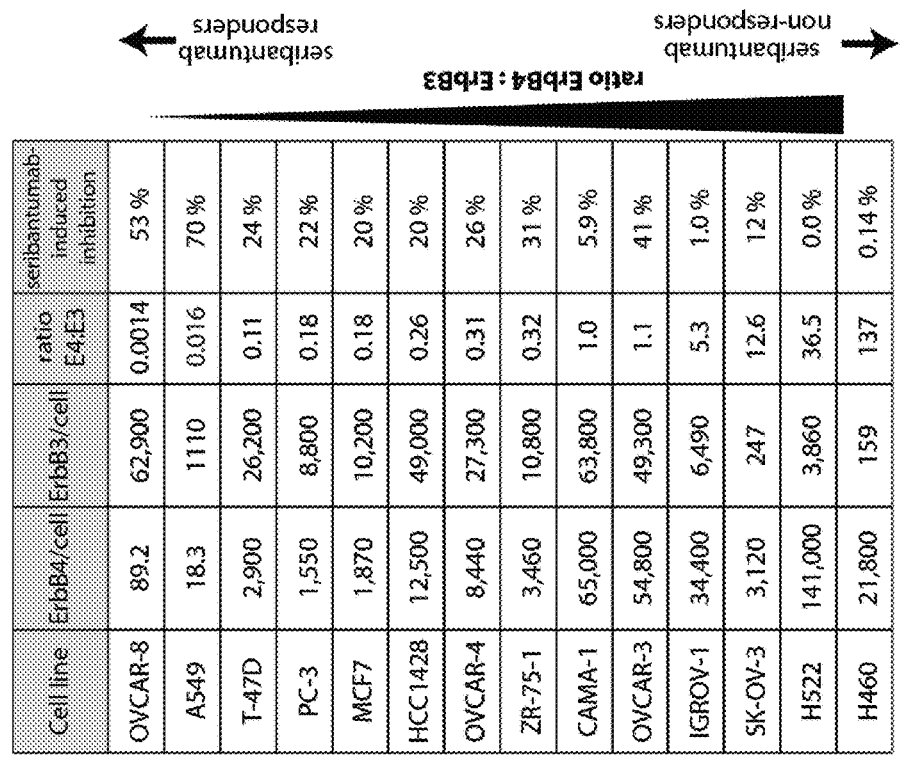
FIGS. 2A-E show the effect of seribantumab on HRG-stimulated cell proliferation in a panel of NCI-60 cell lines with different ErbB4/ErbB3 ratios.
Figure 2B:
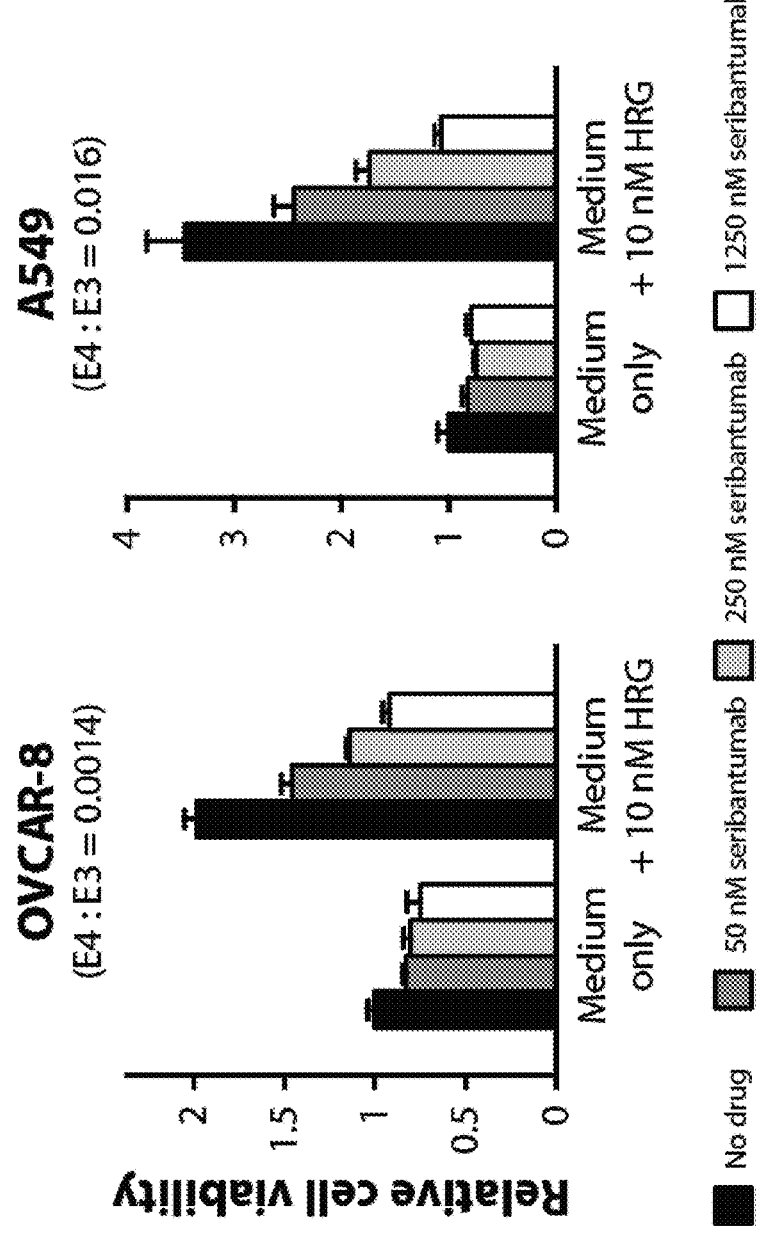
Figure 2C:
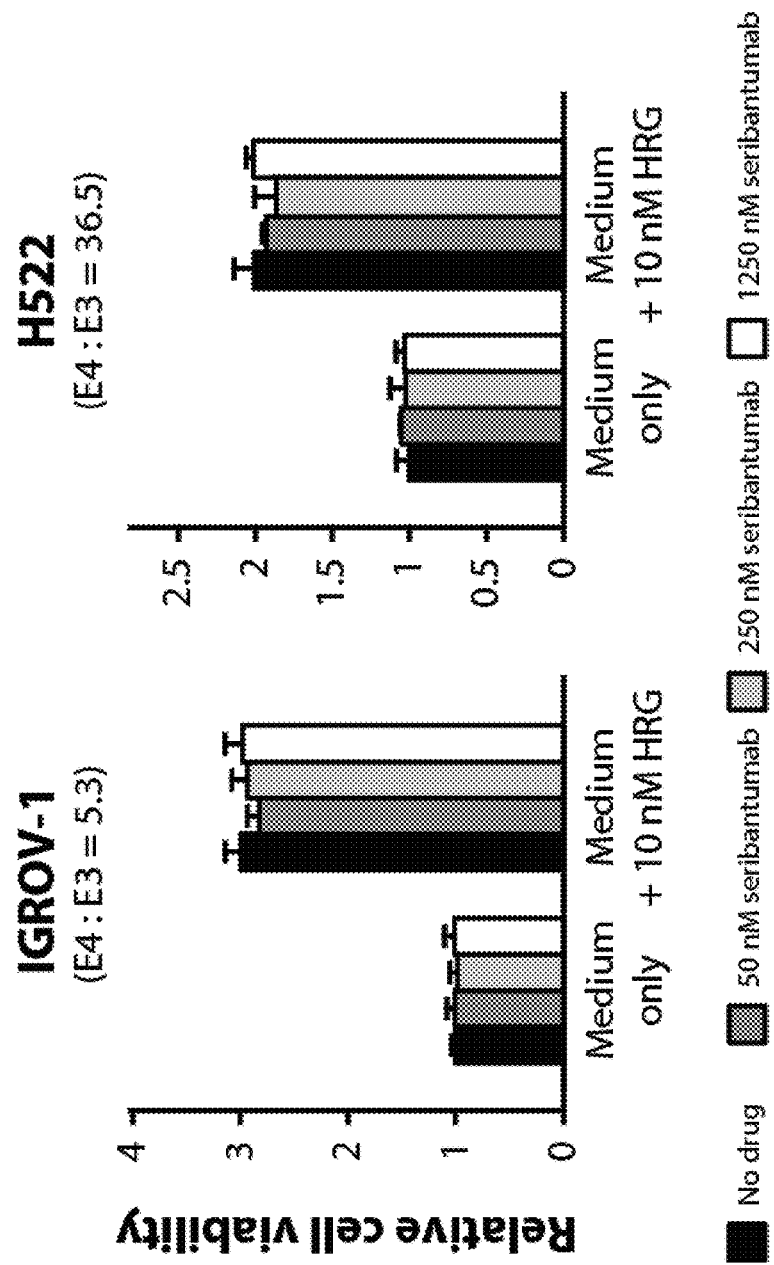
Figure 2D:
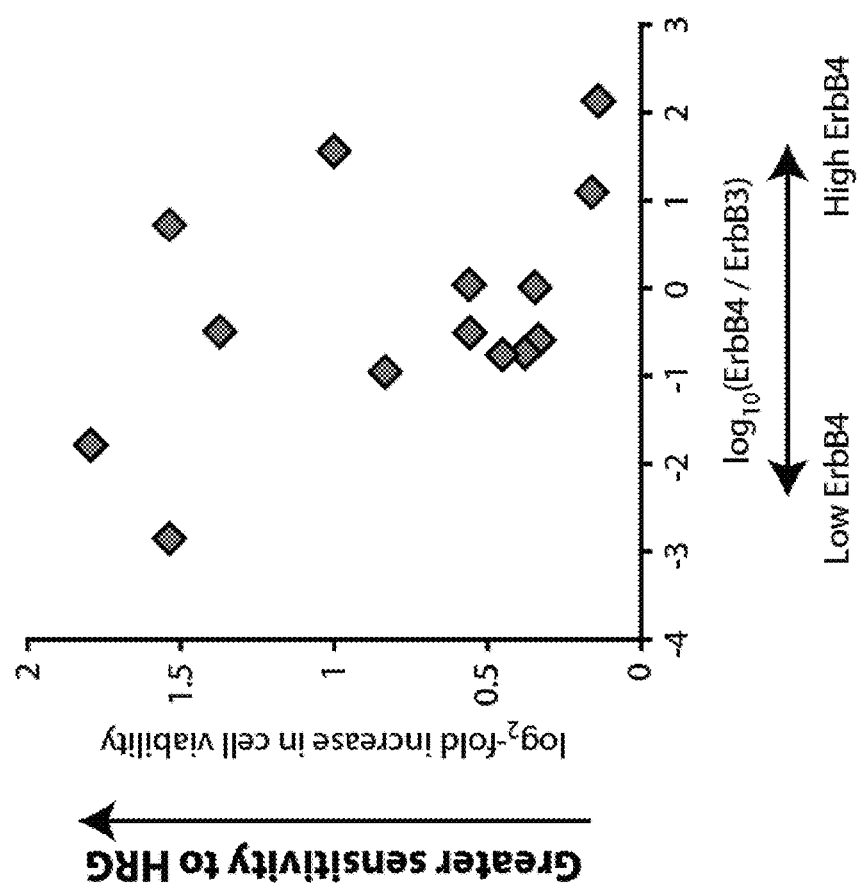
Figure 2E:
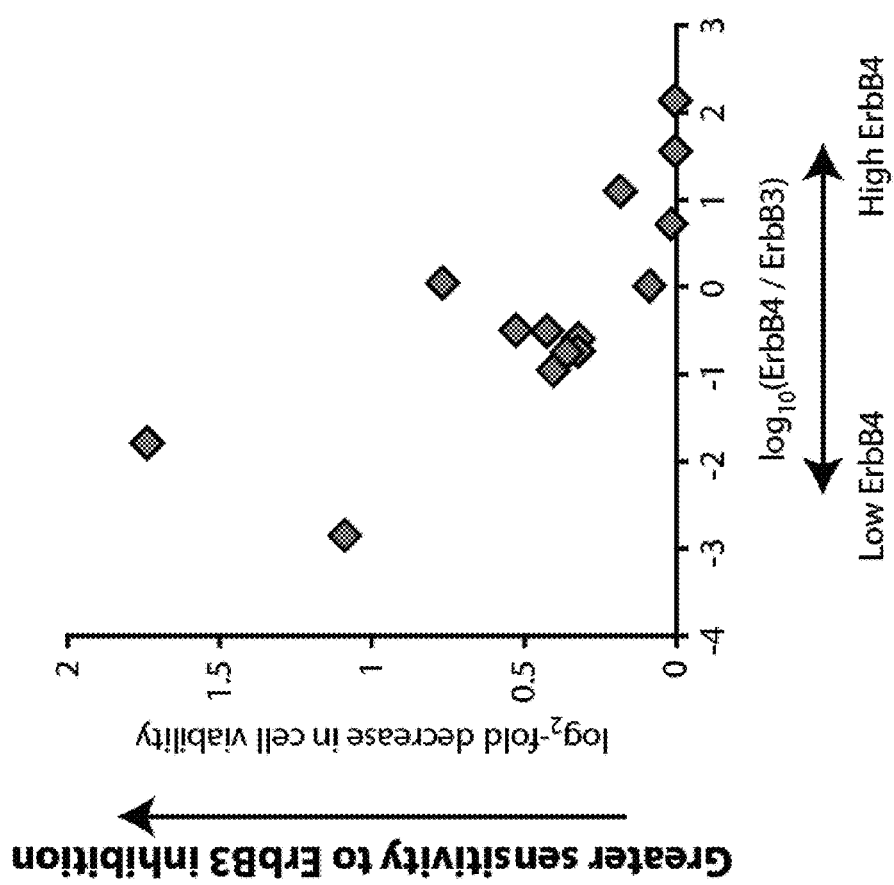

Example 1: Effect of ErbB4/ErbB3 Ratio on Seribantumab Activity in Various Cell Lines To test the inhibitory effect of seribantumab, a panel of human cell lines with different ErbB4/ErbB3 ratios was selected from the NCI-60 panel (FIG. 2A). A CTG assay was used as the readout to test the effect of ErbB4/ErbB3 ratio on the ability of seribantumab to inhibit HRG-induced cell proliferation. Inhibition was defined as a 20% reduction in cell proliferation (via CTG) by 1.25 µM of seribantumab as compared to control, wherein a cell line with 20% or more reduction in cell proliferation was identified as a responder, and a cell line with less than 20% inhibition of proliferation was identified as a non-responder. The A549 and OVCAR-8 cell lines (see FIG. 2B) are an example of responder cell lines. Both cell lines have an ErbB4/ErbB3 ratio of less than 0.1, and 10 nM of HRG induced cell proliferation by 4.1-fold and 1.5-fold, respectively. Seribantumab significantly inhibited the HRG stimulation by 70% and 41%, respectively. The IGR-OV1 and H522 cell lines shown in FIG. 2C are an illustrative example of non-responder cells. In both cell lines, each with an ErbB4/ErbB3 ratio of more than 5, 10 nM of HRG induced cell proliferation by 3-fold (IGR-OV1) and 2-fold (H522). However, seribantumab did not block the effect of HRG in either cell line. It was observed that seribantumab non-responder cells all had high ErbB4 levels, and there was a clear correlation between the ErbB4/ErbB3 ratio and the responsiveness of the cells to seribantumab inhibition (FIG. 2C). For all the cell lines analyzed, the ErbB4/ErbB3 ratio didn't affect the sensitivity of cells to HRG stimulation (FIG. 2D), but there was an inverse correlation between the ErbB4/ErbB3 ratio and seribantumab activity (FIG. 2E).

Figure 3:
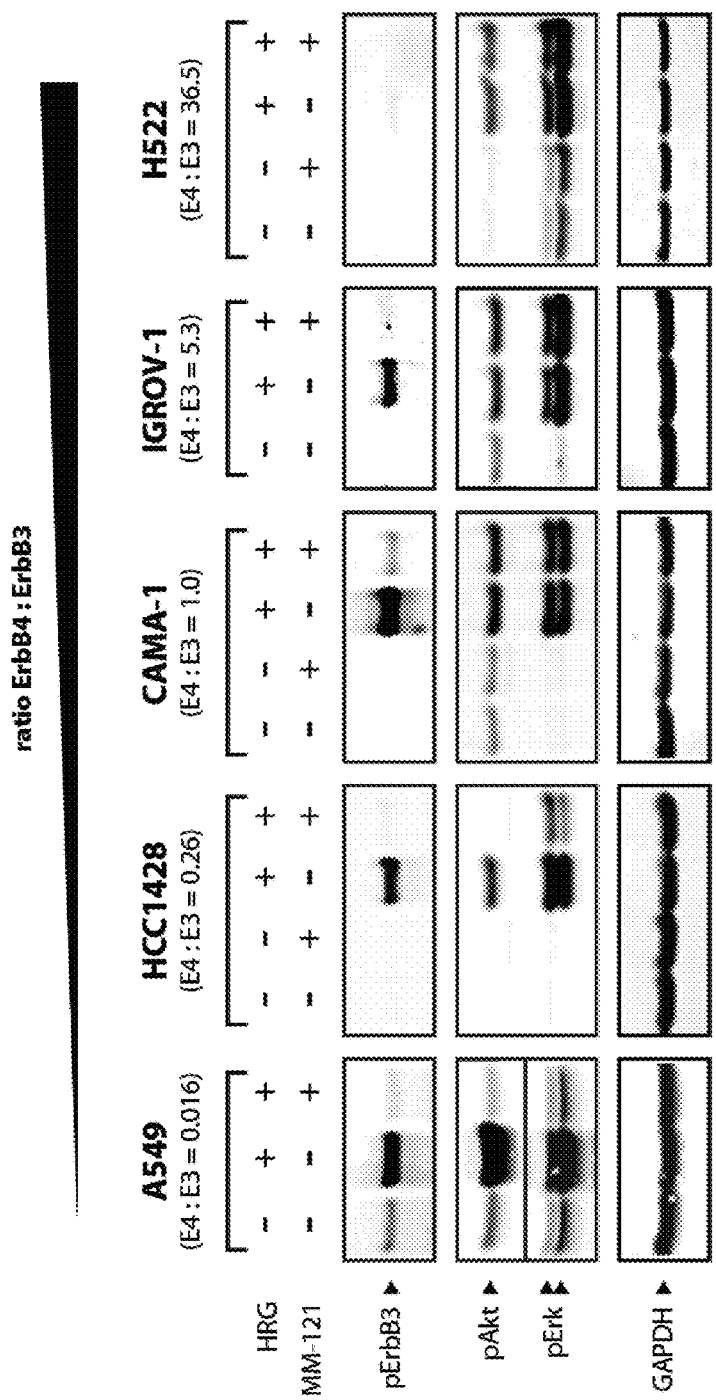
FIG. 3 is a set of images showing the effect of seribantumab on HRG signaling in cells with different ErbB4/ErbB3 ratios. Five cell lines spanning a range of ErbB4/ErbB3 ratios (cells used were A549 (ratio 0.016, lung), HCC-1428 (ratio 0.26, breast), CAMA-1 (ratio 1.0, breast), IGR-OV1 (ratio 5.3, ovarian), and H522 (ratio 36.5, lung)) were pretreated with 250 nM of seribantumab for 1 hour, followed by stimulation with 10 nM of HRG for 10 min. Cells were lysed, and levels of phosopho-ErbB3 (pErbB3), phospho-Akt (pAkt), and phospho-ERK (pERK) were measured by western blotting. GAPDH was used as a loading control.

To examine the mechanism by which the high ErbB4/ErbB3 ratio attenuated seribantumab activity, the effect of the ErbB4/ErbB3 ratio on seribantumab inhibition of HRG-induced signaling was evaluated by western blot. As shown in FIG. 3, seribantumab potently inhibited HRG-induced ErbB3 phosphorylation in all the cell lines. However, in cell lines with low ErbB4/ErbB3 ratios, such as A549 and HCC1428, seribantumab treatment only inhibited events downstream of HRG induced signaling, such as production of pAkt and/or pERK. In contrast, seribantumab treatment was ineffective in cell lines with high ErbB4/ErbB3 ratios such as IGR-OV1 and H522. Seribantumab itself did not show any ErbB3 agonist effect (FIG. 3). Both the phenotypic data and signaling data support the hypothesis that the high ErbB4/ErbB3 ratios attenuated seribantumab activity.

Figure 4A:
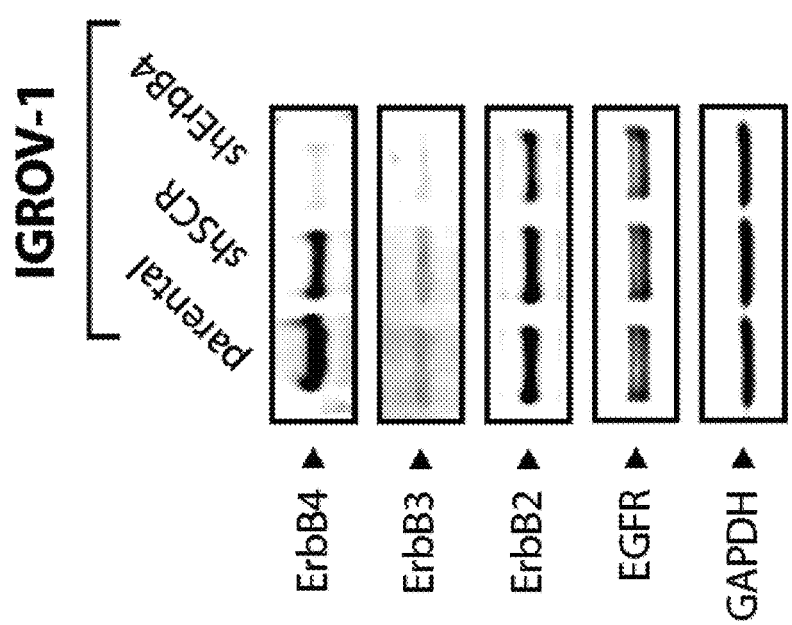
FIGS. 4A-C demonstrate that ErbB4 depletion renders IGR-OV1 cells sensitive to seribantumab. IGR-OV1 cells were infected with lentivirus containing either ErbB4 short hairpin RNA (shErbB4) or scrambled sequence shRNA ("shSCR") as a negative control. The "parental" cell line refers to the wild-type cells. Puromycin resistant cells were collected and analyzed by western blot.
Figure 4B:
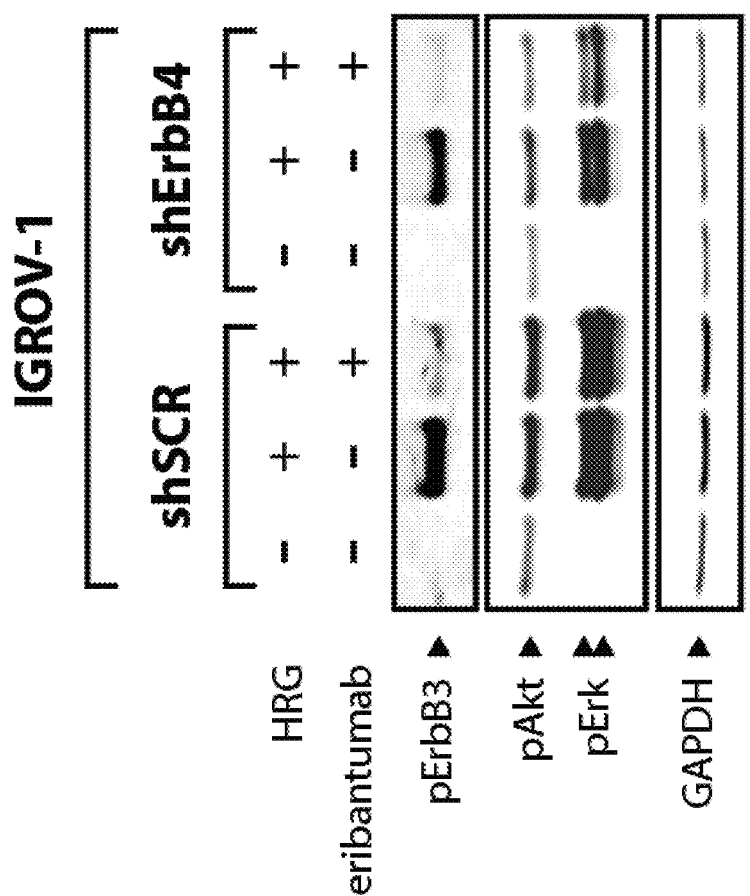
Figure 4C:
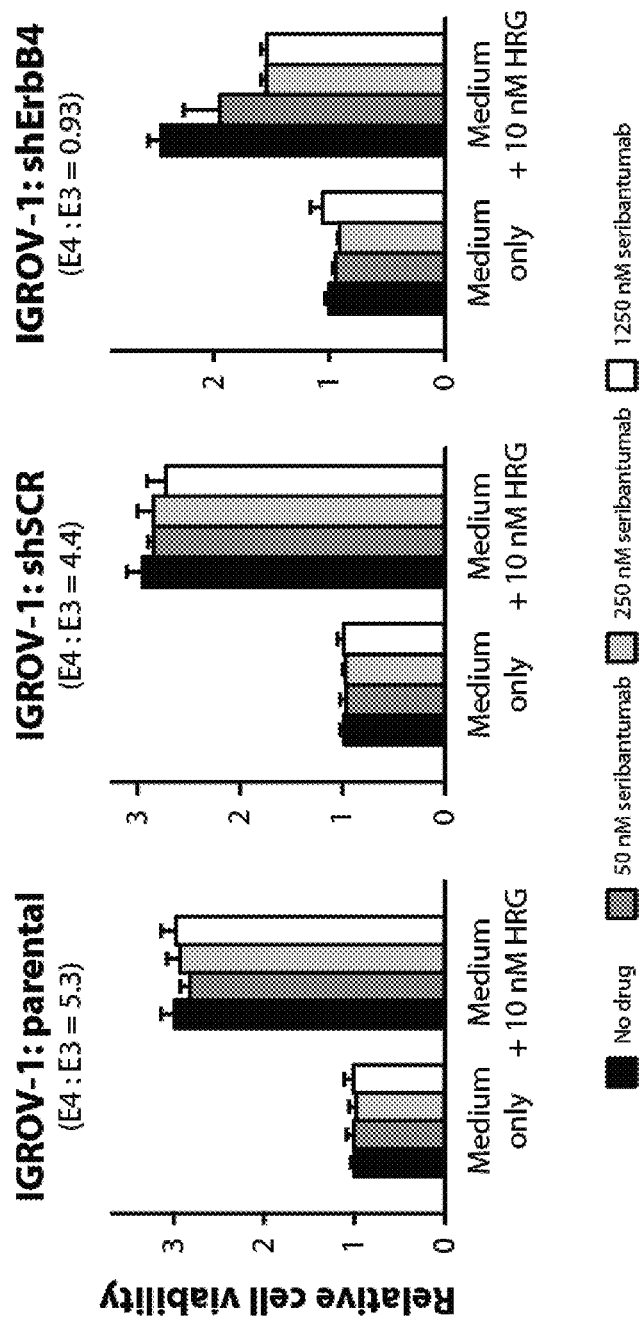
Figure 4D:
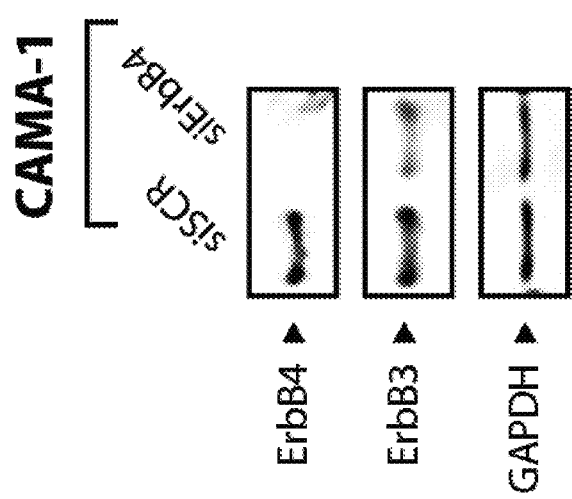
FIGS. 4D-G demonstrate that ErbB4 depletion also renders CAMA-1 cells sensitive to seribantumab. CAMA-1 cells were transduced with lentivirus containing ErbB4 short interfering RNA (siRNA; "siErbB4"), ErbB4 short hairpin RNA ("shErbB4"), scrambled sequence siRNA ("siSCR") or scrambled sequence shRNA ("shSCR"). Both siErbB4 and shErbB4 significantly down-regulated ErbB4 (western blot analysis, FIGS. 4D and 4F) and these cells, when treated with HRG, subsequently had a greater response to treatment with seribantumab (CTG assay, FIGS. 4E and 4G).

Example 2: Effect of Knocking Down ErbB4 in High ErbB4/ErbB3 Ratio Cells on Seribantumab Activity—In Vitro Study The effect of ErbB4/ErbB3 ratio on seribantumab activity was tested using ErbB4-engineered cells. To determine whether seribantumab non-responders with a high ErbB4/ErbB3 ratio could become responders by reducing expression of (knocking down) ErbB4 protein, ErbB4 knockdown cells were created by treating IGR-OV1 and CAMA-1 cells with sh/siRNA. As shown in the western blot image in FIG. 4A, the expression of ErbB4 sequence-specific shRNA dramatically knocked down ErbB4 expression in IGR-OV1 cells by more than 80% without interfering with other ErbB family members. Cells transfected with scrambled sequence shRNA were used as a control. The ErbB4/ErbB3 ratio of IGR-OV1-parental, scrambled sequence and ErbB4 knockdown were 5.3, 4.4, and 0.93, respectively. These data show correlation between shRNA-induced ErbB4 down-regulation and the ability of seribantumab to inhibit HRG induced downstream production of pAkt and pERK (FIG. 4B). Next the, effect of seribantumab on HRG induced proliferation among these cell lines was investigated. Consistent with the data shown in FIGS. 2A-E, while seribantumab was ineffective at inhibiting HRG-induced cell growth in parental and scrambled sequence IGR-OV1 cells with high ErbB4/ErbB3 ratios, it dose-dependently inhibited HRG-induced cell growth in ErbB4 knockdown IGR-OV1 cells (FIG. 4C).

Figure 4E:
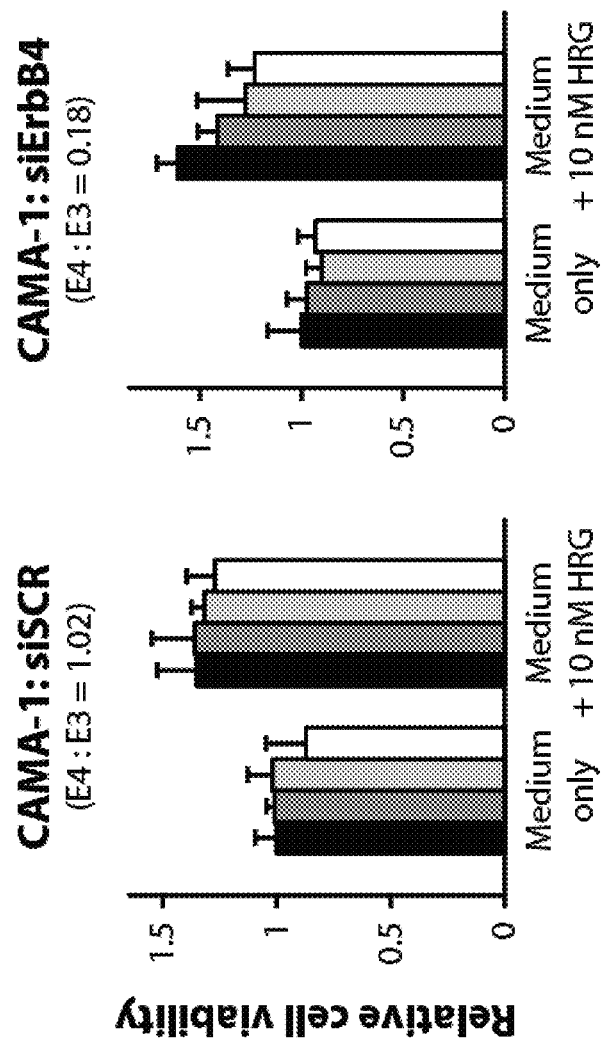
Figure 4F:
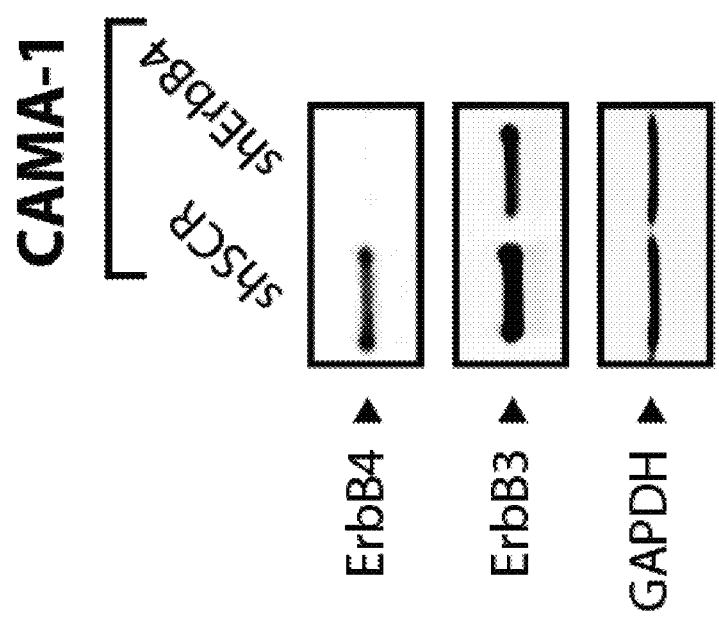
Figure 4G:
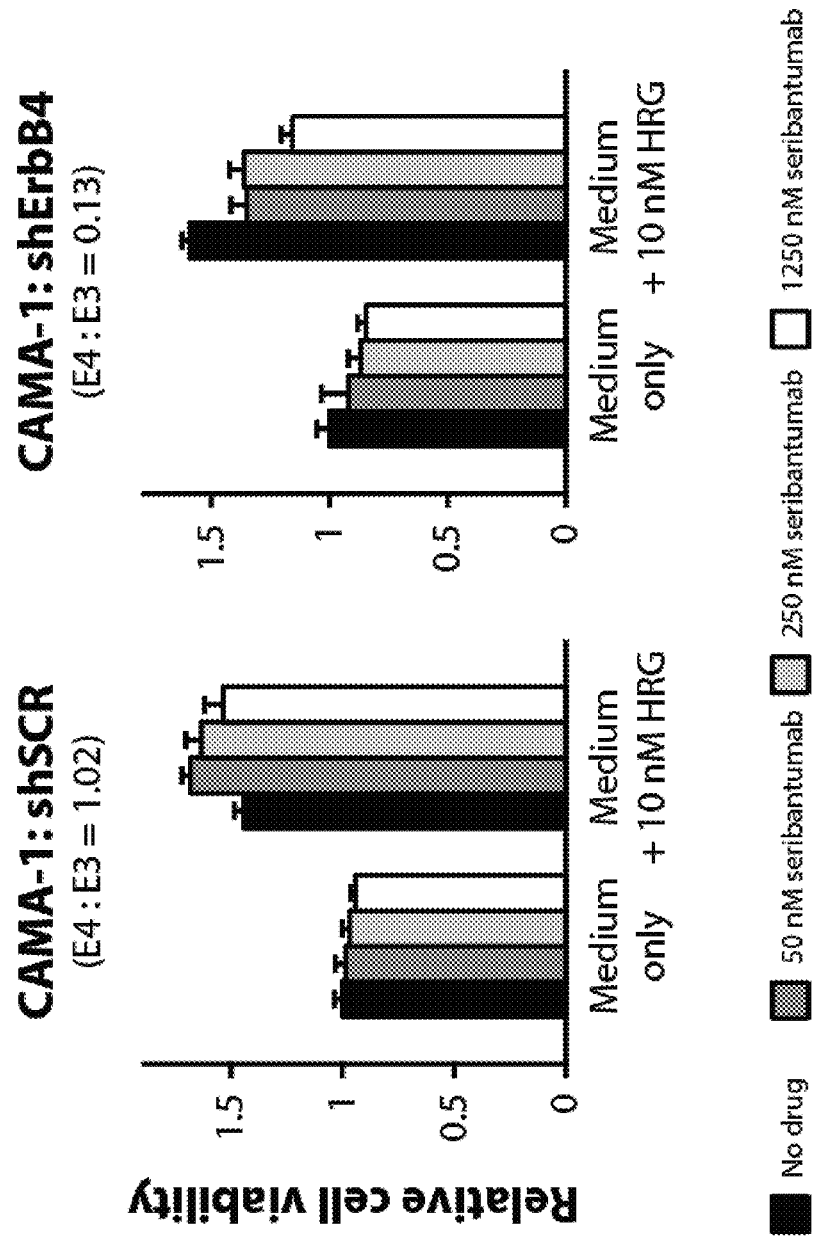

Similar results were obtained from CAMA-1 cells as well (FIG. 4D-G). Both ErbB4 siRNA and shRNA significantly down-regulated ErbB4 (FIGS. 4D and 4F) and these cells subsequently had a greater response to treatment with seribantumab (FIGS. 4E and 4G). These data show that decreasing the ErbB4/ErbB3 ratio in seribantumab non-responder cells by knocking down ErbB4 rescued the ability of cells respond to seribantumab.

Figure 5A:
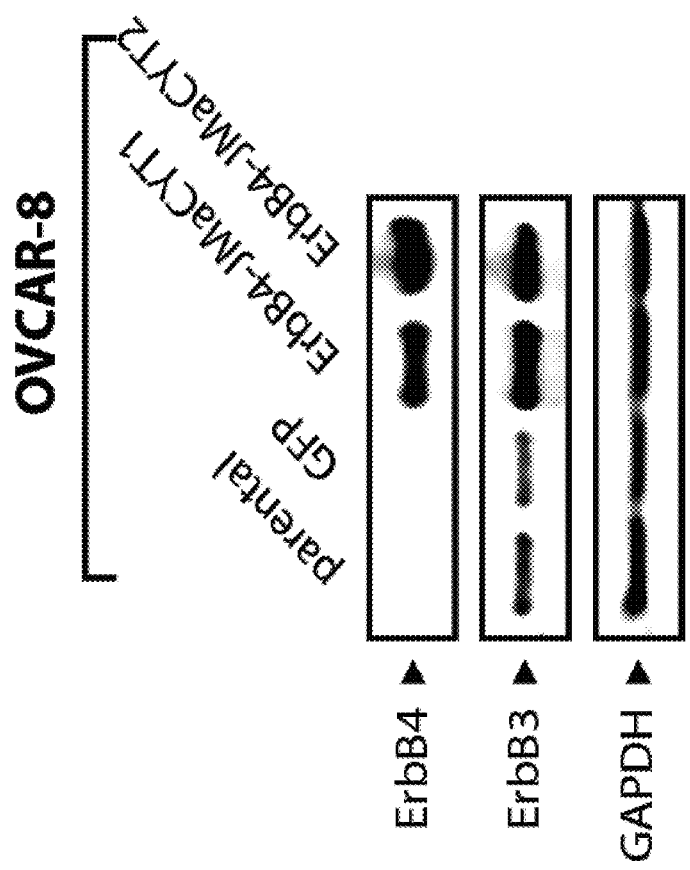
FIGS. 5A-G show that overexpression of ErbB4 renders OVCAR-8 cells resistant to seribantumab. OVCAR-8 cells were infected with lentivirus encoding ErbB4-JMaCYT1 (the ErbB4 isoform comprising JMa and CYT1 splice variants), ErbB4-JMaCYT2 (the ErbB4 isoform comprising JMa and CYT2 splice variants), or GFP as a control. Puromycin resistant cells were selected and tested.
Figure 5B:
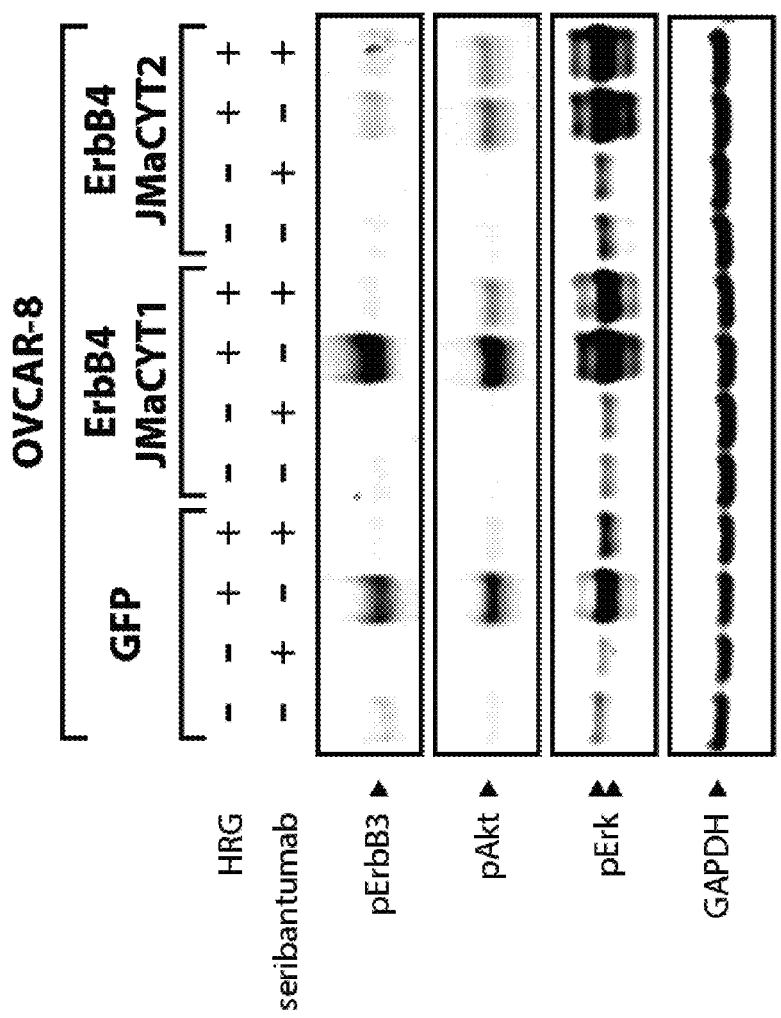

Example 3: Effect of ErbB4 Overexpression on Seribantumab Activity—In Vitro Study To further test the relationship of the ErbB4/ErbB3 ratio to seribantumab activity, ErbB4 was overexpressed in the responder cell line OVCAR-8 which has a low ErbB4/ErbB3 ratio. Cells were transduced with a lentivirus vector encoding either the JMaCYT1 isoform of ErbB4 or the JMaCYT2 isoform of ErbB4 and cultured in puromycin selection medium. Cells transduced with GFP-encoding lentivirus vector were used as control. The ErbB4 expression level in pooled cell lines was tested by western blot. Both ErbB4 isoforms were highly expressed compared to that in parental and GFP-expressing control cells, as shown in FIG. 5A. The ErbB4/ErbB3 ratio of OVCAR-8 parental, GFP-expressing control, ErbB4 JMaCYT1, and JMaCYT2-expressing cell lines were 0.00014, 0.00022, 1.8, and 2.6, respectively. Increasing the ErbB4/ErbB3 ratio significantly decreased the ability of seribantumab to inhibit HRG-induced pAkt and pERK (FIG. 5B). Seribantumab significantly inhibited HRG induced pAkt and pERK in GFP control cells, but not in ErbB4 JMaCYT1- and ErbB4 JMaCYT2-expressing cells with high ErbB4/ErbB3 ratios.

Figure 5C:
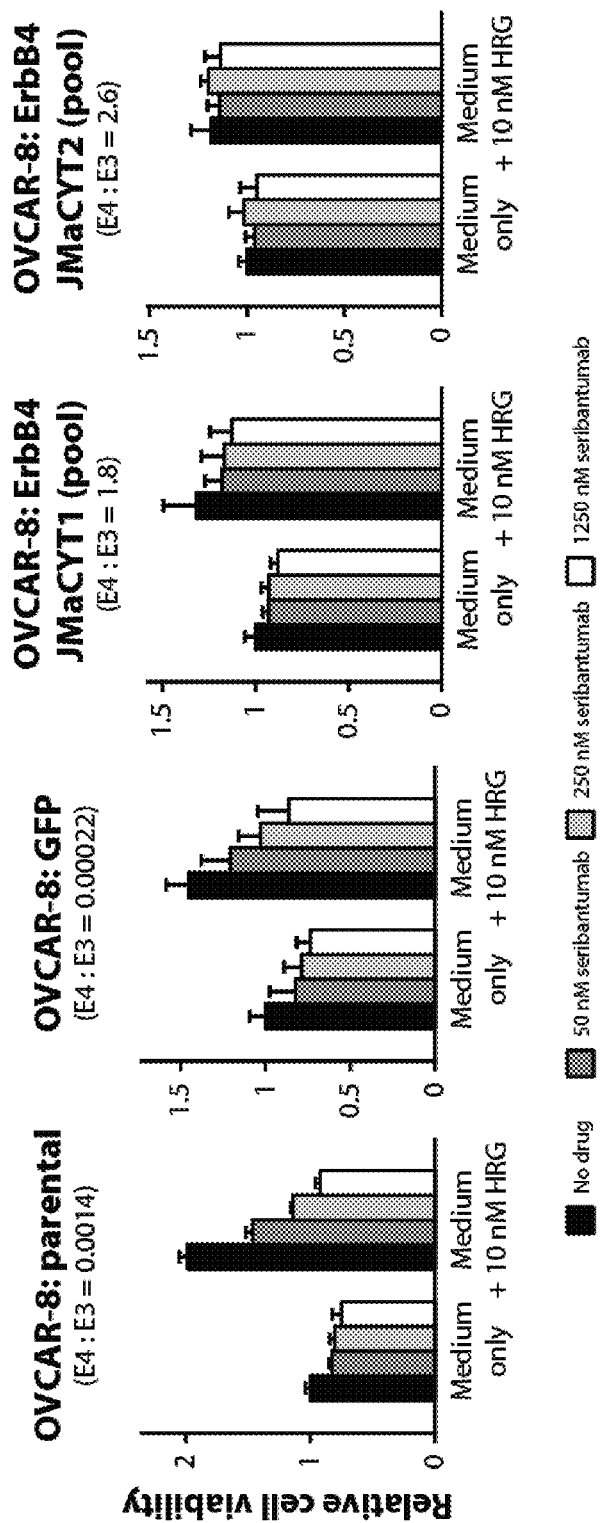
Figure 5D:
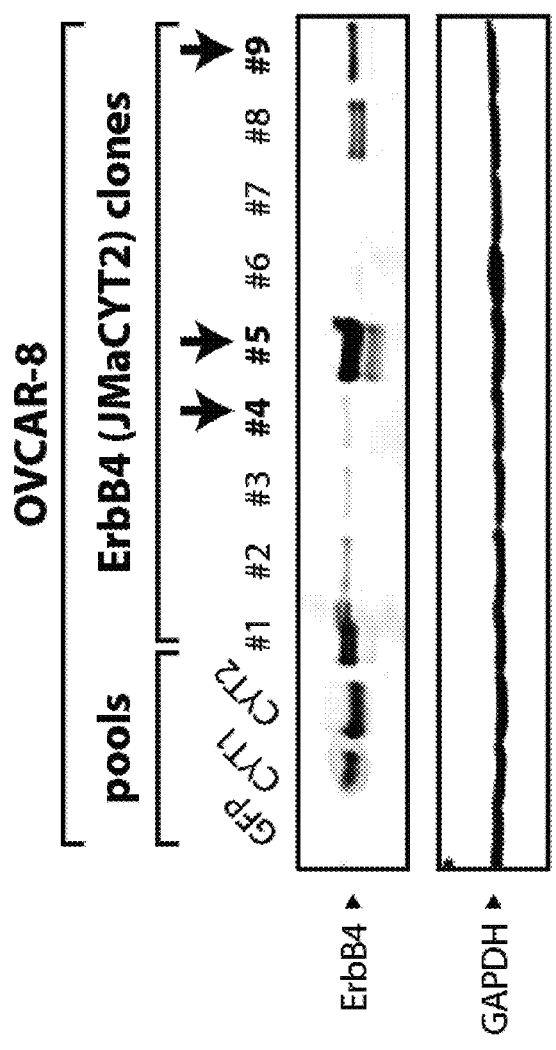
Figure 5E:
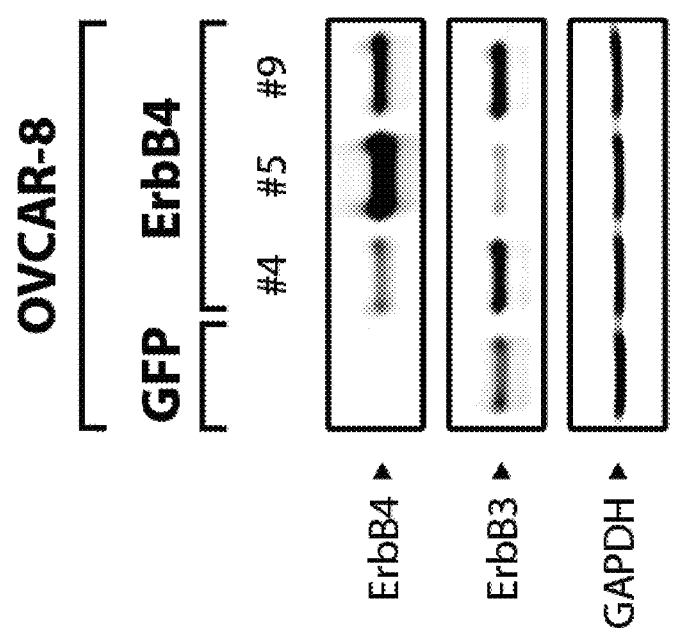
Figure 5F:
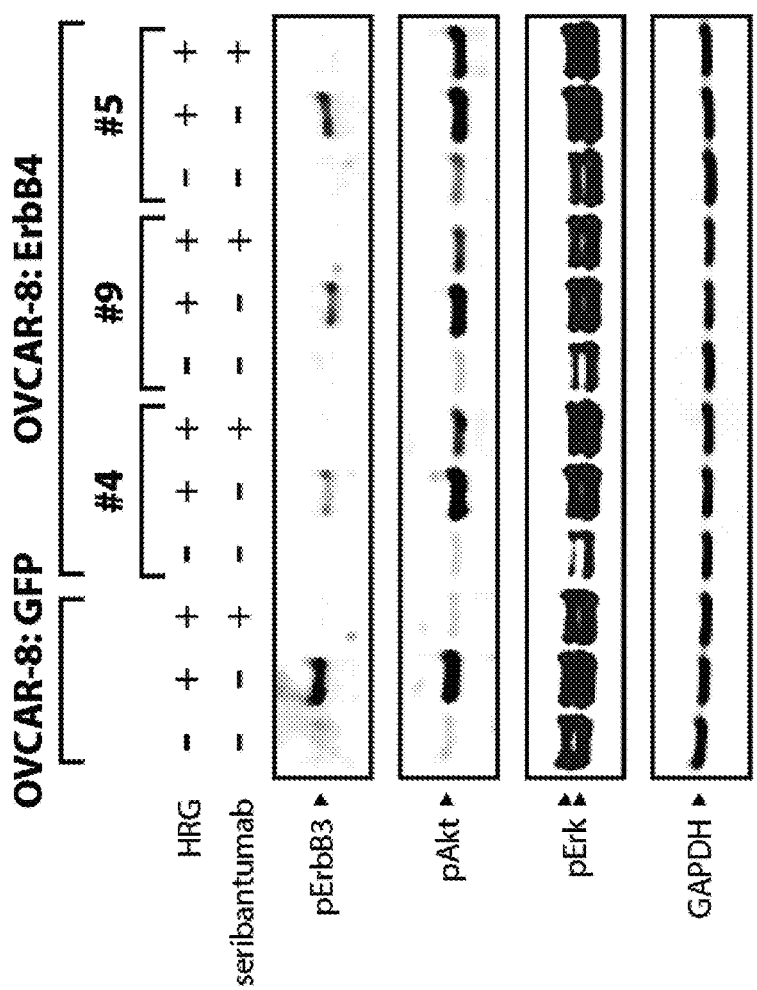
Figure 5G:
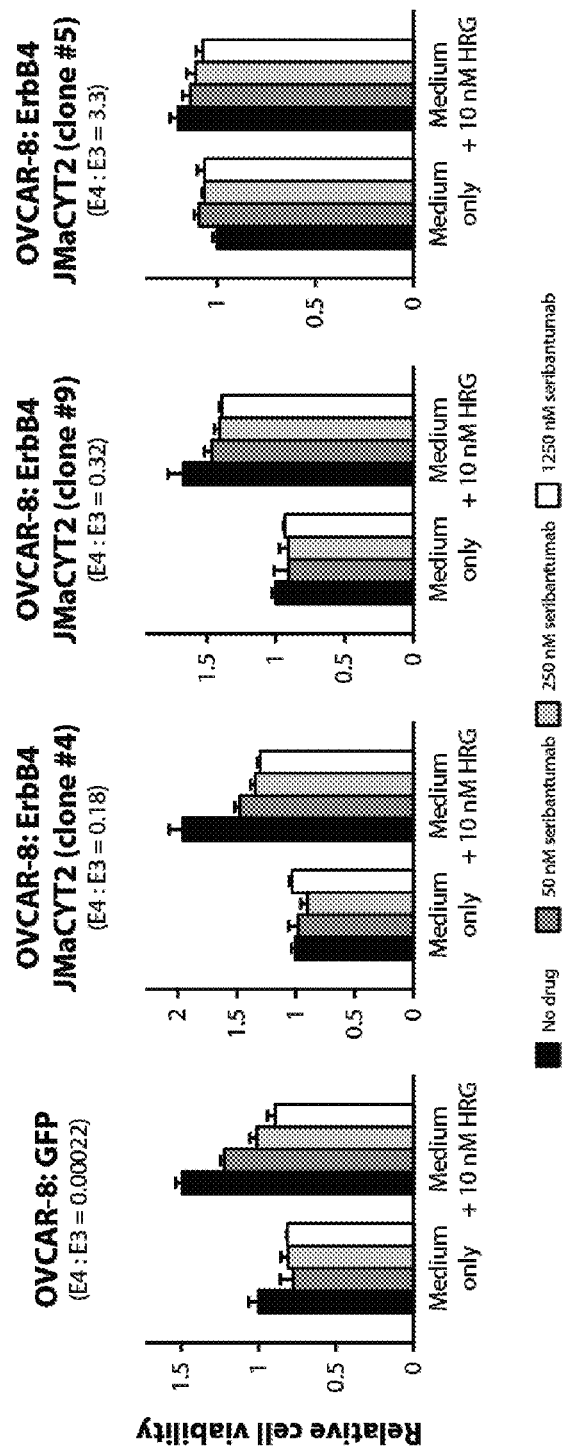

Next, the impact of increasing the ErbB4/ErbB3 ratio on seribantumab ability to inhibit cell growth was examined. In parental and GFP-expressing control cells with a very low ErbB4/ErbB3 ratio (<0.01), seribantumab at 1.25 µM inhibited HRG induced cell proliferation by 53.7% and 40.8%, respectively. But for both OVCAR-8-JMaCYT1 and OVCAR-8-JMaCYT2 cells, seribantumab inhibited less than 20% of HRG-induced cell growth (FIG. 5C), indicating that increasing the ErbB4/ErbB3 ratio by overexpressing ErbB4 made the OVCAR-8 cells less sensitive to seribantumab. It was observed that while OVCAR-8-JMaCYT2 cells became resistant to seribantumab, they also lost sensitivity to HRG stimulation. In order to determine whether this might be due to the heterogeneity of the pooled cell population (possibly containing some cells with unknown transfection-mediated changes that caused cells to be unresponsive to HRG), cells were collected from single clones of the pooled cells in order to produce a homogenous cell culture. The selected clones showed a high degree of variability in the amount of ErbB4, as analyzed by western blot (FIG. 5D), suggesting that the heterogeneity in the pooled cell lines may have been due to variations in the ErbB4 expression level. For ongoing experiments, clones #4, #5, and #9, representing ErbB4 low, high, and medium over-expressing levels, respectively, were tested for their response to HRG stimulation and sensitivity to seribantumab inhibition. The ErbB4 and ErbB3 levels were determined for each clone (FIG. 5E) and the ErbB4/ErbB3 ratio was measured (see FIG. 5G). First, a set of CTG assays was performed to determine the ability of seribantumab to inhibit cell proliferations in the different expression clones. As shown in FIG. 5G, 10 nM HRG stimulated cell growth in all cell lines but clone#5 (high ErbB4/ErbB3 ratio), which may have contributed to the HRG unresponsiveness of the pooled OVCAR-8-JMaCYT2 cells shown in FIG. 5C. Seribantumab inhibited HRG-induced cell growth by 49% in OVCAR8-GFP cells, 45% in low ErbB4 expression clone #4, 25% in medium ErbB4 expression clone #9, and 8% in high ErbB4 expression clone #5, indicating a clear correlation between the ErbB4/ErbB3 ratio and the ability of seribantumab to inhibit HRG-induced cell growth (FIG. 5G). Similar results were obtained when signaling was examined by western blot; HRG treatment resulted in phosphorylation of ErbB3, Akt, and ERK in all the cell lines. While seribantumab almost completely inhibited HRG-induced production of pErbB3 regardless of ErbB4 level, the ability of seribantumab to inhibit the production of pAkt and pERK was attenuated with increased ErbB4 level (FIG. 5F). Clone#9 was further tested in the in vivo xenograft model described below in Example 5.

Figure 6A:
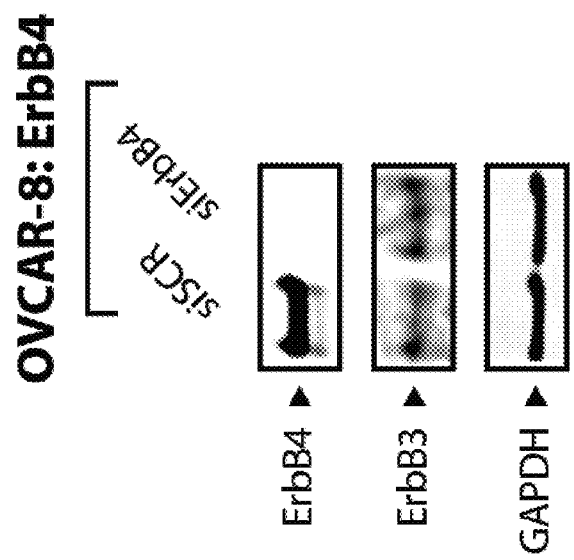
FIGS. 6A-C show that ErbB4 depletion re-sensitizes ErbB4-overexpressing OVCAR-8 cells to seribantumab. In ErbB4 JMaCYT2 over-expressing OVCAR-8 cells, ErbB4 was knocked down with ErbB4 siRNA to test the sufficiency of ErbB4 to cause resistance to seribantumab. Scrambled sequence siRNA was used as control.
Figure 6B:
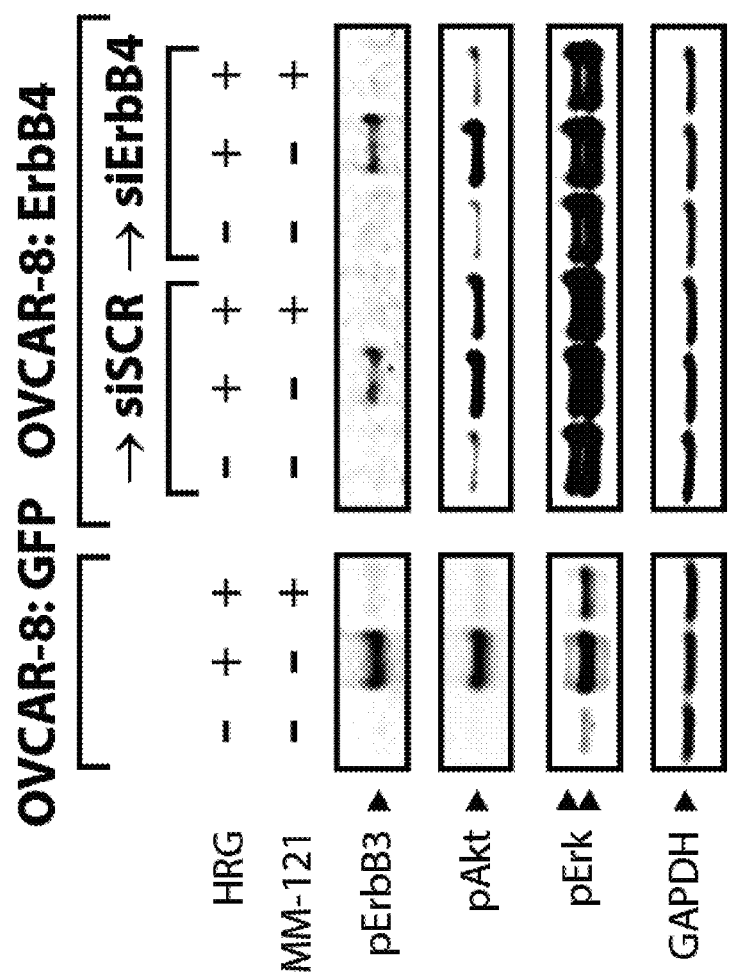
Figure 6C:
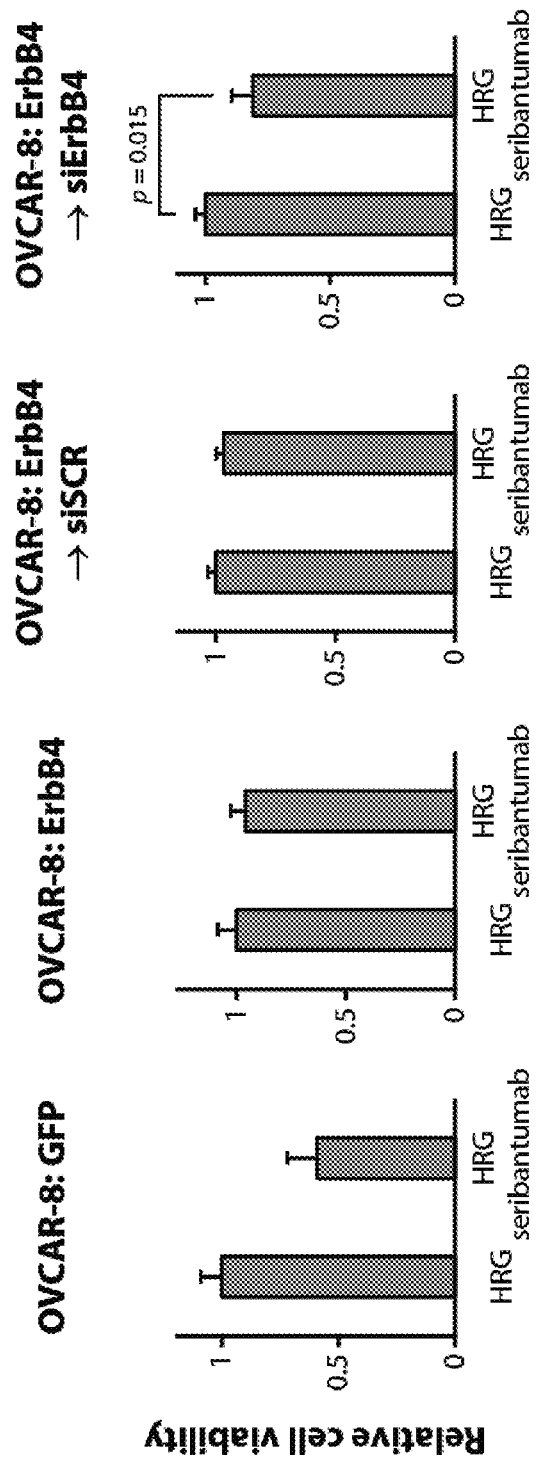

Example 4: Rescue Effect of Knocking Down ErbB4 with siRNA in OVCAR8-ErbB4JMa CYT2 Cells As described above for FIG. 5A, overexpressing ErbB4 in OVCAR-8 cells also changed the level of ErbB3 and other signaling pathway members. In order to confirm that the observed effect was due to the presence of ErbB4, ErbB4 was then transiently knocked down by using ErbB4 sequence-specific siRNA in OVCAR-8-ErbB4JMaCYT2 cells to determine if seribantumab sensitivity could be rescued. Scrambled sequence siRNA was used as a control (FIG. 6A). As shown in FIG. 6B, in scrambled sequence cells with high ErbB4, seribantumab could not inhibit HRG-induced pAkt and pERK; whereas in ErbB4 cells expressing the ErbB4 siRNA, seribantumab inhibited HRG-induced pAkt and pERK to a similar extent compared with GFP control cells. The data detected by the CTG assay also showed that seribantumab inhibited HRG-induced cell growth in ErbB4 siRNA transfected cells, but not in scrambled sequence siRNA control (FIG. 6C). Both the signaling data and the CTG assay data showed that knockdown of ErbB4 in OVCAR-8-ErbB4 cells re-sensitized the cells to seribantumab, indicating that ErbB4 is sufficient to cause seribantumab resistance in OVCAR-8 cells.

Example 5: Effect of ErbB4/ErbB3 Ratio on Seribantumab Activity In Vivo

Figure 7A:
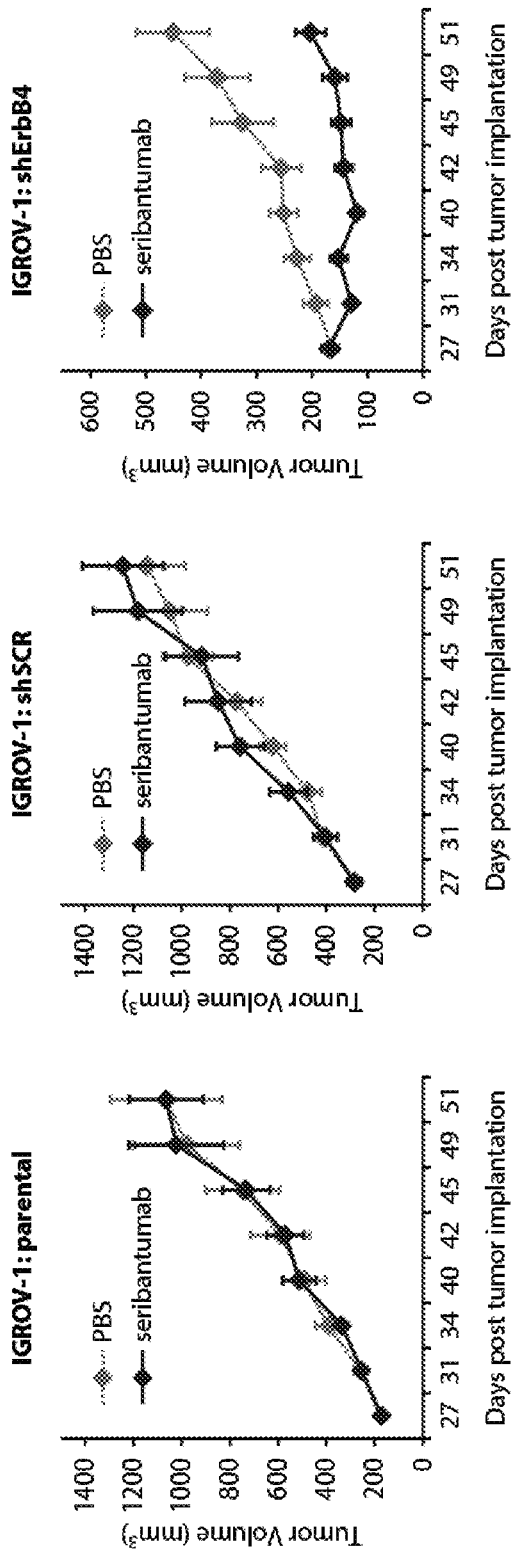
FIGS. 7A-B show the effect of seribantumab on the in vivo tumor growth of Erbb4 engineered cell lines. IGR-OV1 (FIG. 7A) or OVCAR8 (FIG. 7B) cells were subcutaneously injected into nude mice to establish tumor xenografts. Once tumors reached approximately ~200 mm$^3$ in volume, the mice were randomized into treatment groups to receive either 600 μg seribantumab every 3 days (Q3D) or PBS (Q3D) as a control. Tumor dimensions were measured twice a week and the tumor volumes were calculated using the formula: $\pi/6 \times L \times W^2$.
Figure 7B:
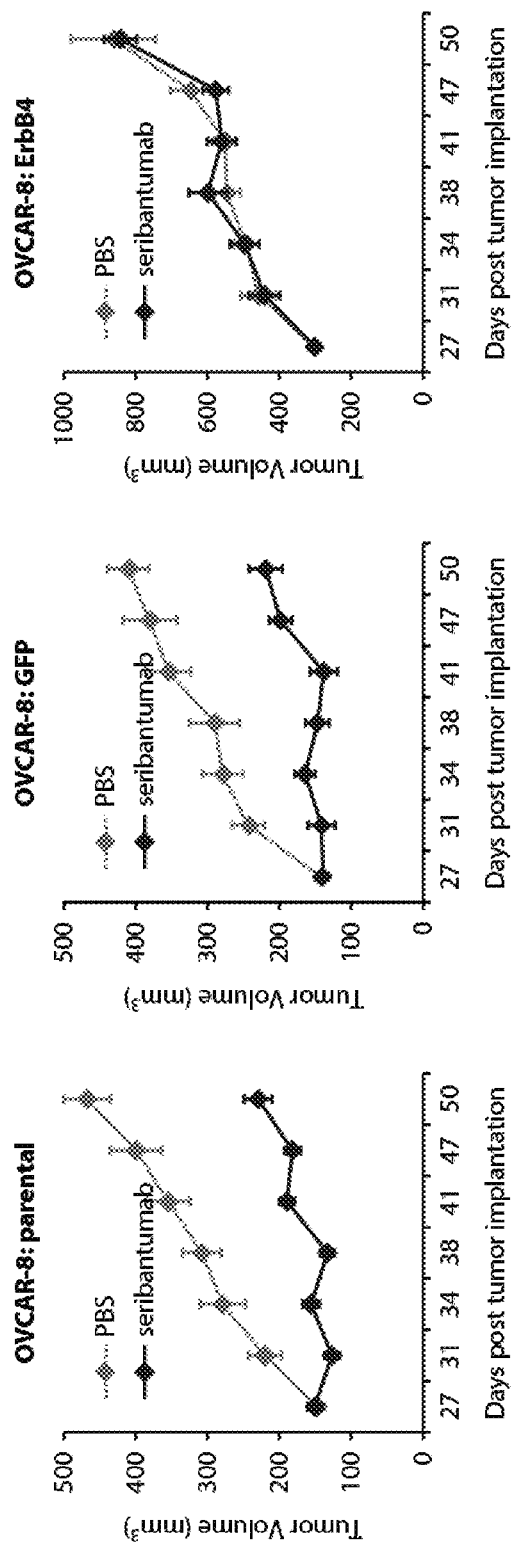

In order to test if the observed effect of the ErbB4/ErbB3 ratio in vitro might also be observed in an in vivo setting, a xenograft study was performed using ErbB4 stable knockdown IGR-OV1 cells and ErbB4 stable overexpressing OVCAR-8 cells as described above. In each model, seribantumab activity was compared among parental cells, engineered control cells (either scrambled sequence or GFP overexpression), and ErbB4 engineered cells. The tumor-bearing mice were treated with either PBS as a control or 600 µg/kg of seribantumab. For the IGR-OV1-ErbB4 knockdown model, consistent with in vitro data, treatment with seribantumab had no effect on parental IGR-OV1 or IGR-OV1-scrambled sequence tumor growth, whereas tumor cell proliferation from ErbB4 knockdown-IGR-OV1 was significantly inhibited by seribantumab (FIG. 7A). In the OVCAR8-ErbB4 over-expression model, tumor growth from both parental and GFP-expressing OVCAR-8 cells was significantly inhibited by seribantumab, whereas tumor growth from OVCAR-8-ErbB4-expressing clone #9 was resistant to seribantumab treatment (FIG. 7B).

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every U.S., international, or other patent or patent application or publication referred to herein is hereby incorporated herein by reference in its entirety.

SEQUENCE SUMMARY

| SEQ ID NO: | DESIGNATION | SEQUENCE |
|---|---|---|
| 1 | Heavy Chain CDR1 (CDRH1) of Seribantumab Protein | His Tyr Val Met Ala |
| 2 | Heavy Chain CDR2 (CDRH2) of Seribantumab Protein | Ser Ile Ser Ser Ser Gly Gly Trp Thr Leu Tyr Ala Asp Ser Val Lys Gly |
| 3 | Heavy Chain CDR3 (CDRH3) of Seribantumab Protein | Gly Leu Lys Met Ala Thr Ile Phe Asp Tyr |
| 4 | Light Chain CDR1 (CDRL1) of Seribantumab Protein | Thr Gly Thr Ser Ser Asp Val Gly Ser Tyr Asn Val Val Ser |
| 5 | Light Chain CDR2 (CDRL2) of Seribantumab Protein | Glu Val Ser Gln Arg Pro Ser |
| 6 | Light Chain CDR3 (CDRL3) of Seribantumab Protein | Cys Ser Tyr Ala Gly Ser Ser Ile Phe Val Ile |

What is claimed is:

1. A method of treating a patient having a heregulin positive (HRG+) cancer with a solid tumor having a ratio of expressed ErbB4 to ErbB3 of less than 1.3, wherein the expressed ErbB4 and ErbB3 are each detected by RNA in situ hybridization (RNA-ISH) or by RT-PCR, the method comprising: administering a therapeutically effective amount of an anti-ErbB3 antibody to the patient, wherein the anti-ErbB3 antibody comprises CDRH1, CDRH2, and CDRH3 sequences comprising the amino acid sequences set forth in SEQ ID NO:1 (CDRH1), SEQ ID NO:2 (CDRH2), and SEQ ID NO:3 (CDRH3); and CDRL1, CDRL2, and CDRL3 sequences comprising the amino acid sequences set forth in SEQ ID NO:4 (CDRL1), SEQ ID NO:5 (CDRL2), and SEQ ID NO:6 (CDRL3).

2. The method of claim 1, wherein the tumor is a NSCLC tumor.

3. The method of claim 1, wherein the tumor is a melanoma tumor.

4. The method of claim 1, wherein the tumor is a breast tumor.

5. The method of claim 1, wherein the tumor is an ovarian tumor.

6. The method of claim 1, wherein the tumor is platinum-resistant or refractory.

7. The method of claim 1, wherein the anti-ErbB3 antibody is seribantumab.

8. A method of treating a patient diagnosed with a heregulin positive (HRG+) solid tumor having a ratio of expressed ErbB4 to ErbB3 of less than 1.3, wherein the expressed ErbB4 to ErbB3 are each detected by RNA in situ hybridization (RNA-ISH) or by RT-PCR, the method comprising: administering a therapeutically effective amount of an anti-ErbB3 antibody to the patient, wherein the anti-ErbB3 antibody comprises CDRH1, CDRH2, and CDRH3 sequences comprising the amino acid sequences set forth in SEQ ID NO:1 (CDRH1), SEQ ID NO:2 (CDRH2), and SEQ ID NO:3 (CDRH3); and CDRL1, CDRL2, and CDRL3 sequences comprising the amino acid sequences set forth in SEQ ID NO:4 (CDRL1), SEQ ID NO:5 (CDRL2), and SEQ ID NO:6 (CDRL3).

9. The method of claim 8, wherein the cancer is NSCLC.

10. The method of claim 8, wherein the cancer is melanoma.

11. The method of claim 8, wherein the cancer is breast cancer.

12. The method of claim 8, wherein the cancer is an ovarian cancer.

13. The method of claim 8, wherein the anti-ErbB3 antibody is seribantumab.

14. A method of treating a patient diagnosed with a cancer selected from the group consisting of: non-small cell lung cancer (NSCLC), melanoma, breast cancer, and ovarian cancer, the cancer having a heregulin positive (HRG+) solid tumor having a ratio of expressed ErbB4 to ErbB3 of less than 1.3, wherein the expressed ErbB4 and ErbB3 are each detected by RNA in situ hybridization (RNA-ISH) or by RT-PCR, and the method comprises administering a therapeutically effective amount of seribantumab to the patient.

15. The method of claim 14, wherein the breast cancer is a HRG+, ER+, PR+ and HER2 negative breast cancer.

16. The method of claim 14, wherein the cancer is a NSCLC cancer.

17. The method of claim 14, wherein the cancer is an ovarian cancer.

18. The method of claim 14, wherein the cancer is a melanoma cancer.

* * * * *

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

His Tyr Val Met Ala
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ile Ser Ser Ser Gly Gly Trp Thr Leu Tyr Ala Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Lys Met Ala Thr Ile Phe Asp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Gly Thr Ser Ser Asp Val Gly Ser Tyr Asn Val Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Val Ser Gln Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Cys Ser Tyr Ala Gly Ser Ser Ile Phe Val Ile
1               5                   10
```